(12) United States Patent
Hirao et al.

(10) Patent No.: US 10,760,083 B2
(45) Date of Patent: Sep. 1, 2020

(54) DNA APTAMER THAT BINDS TO VWF

(71) Applicant: TAGCYX BIOTECHNOLOGIES INC., Meguro-ku, Tokyo (JP)

(72) Inventors: Ichiro Hirao, Tokyo (JP); Michiko Hirao, Tokyo (JP); Kenichiro Matsunaga, Tokyo (JP)

(73) Assignee: TAGCyx Biotechnologies Inc., Tokyo (JP)

( * ) Notice: Subject to any disclaimer, the term of this patent is extended or adjusted under 35 U.S.C. 154(b) by 174 days.

(21) Appl. No.: 15/771,588

(22) PCT Filed: Oct. 25, 2016

(86) PCT No.: PCT/JP2016/081518
§ 371 (c)(1),
(2) Date: Apr. 27, 2018

(87) PCT Pub. No.: WO2017/073536
PCT Pub. Date: May 4, 2017

(65) Prior Publication Data
US 2018/0305695 A1    Oct. 25, 2018

(30) Foreign Application Priority Data

Oct. 30, 2015 (JP) ................................. 2015-214848

(51) Int. Cl.
| | | |
|---|---|---|
| *C12N 15/11* | (2006.01) | |
| *C12N 15/115* | (2010.01) | |
| *C12Q 1/68* | (2018.01) | |
| *G01N 33/53* | (2006.01) | |
| *A61K 31/7115* | (2006.01) | |
| *A61P 7/02* | (2006.01) | |
| *A61P 9/10* | (2006.01) | |
| *C07K 14/755* | (2006.01) | |

(52) U.S. Cl.
CPC ........ *C12N 15/115* (2013.01); *A61K 31/7115* (2013.01); *A61P 7/02* (2018.01); *A61P 9/10* (2018.01); *C07K 14/755* (2013.01); *C12Q 1/68* (2013.01); *G01N 33/53* (2013.01); *C12N 2310/16* (2013.01); *C12N 2310/333* (2013.01); *C12N 2310/531* (2013.01); *C12N 2320/30* (2013.01)

(58) Field of Classification Search
None
See application file for complete search history.

(56) References Cited

FOREIGN PATENT DOCUMENTS

| EP | 1970445 B1 * | 9/2012 | ............. C07H 19/04 |
|---|---|---|---|
| EP | 2 781 599 A1 | 9/2014 | |
| EP | 3 266 871 A1 | 1/2018 | |

OTHER PUBLICATIONS

Gilbert et al., "First-in-Human Evaluation of Anti-von Willebrand Factor Therapeutic Aptamer ARC1779 in Healthy Volunteers," Circulation, Nov. 19, 2007, 116:2678-2686.
Sadler, J. Evan, "Biochemistry and Genetics of Von Willebrand Factor," Annu. Rev. Biochem., 1998, 67:395-424.
Kimoto et al., "Generation of High Affinity DNA Aptamers by the Expansion of the Genetic Alphabet," Collection Symposium Series, 2014, vol. 14, pp. 97-100.
Siller-Matula et al., "ARC15105 is a Potent Antagonist of Von Willebrand Factor Mediated Platelet Activation and Adhesion," Arterioscler Thrombosis Vascular Biology, 2012, vol. 32, pp. 902-909.
Supplementary European Search Report dated May 17, 2019, in EP 16859766.4.

* cited by examiner

*Primary Examiner* — Ekaterina Poliakova-Georgantas
(74) *Attorney, Agent, or Firm* — Foley & Lardner LLP

(57) ABSTRACT

The purpose of the present invention is to provide an aptamer for vWF, which is superior in a binding ability, a dissociation rate, and/or stability to the conventional nucleic acid aptamers. The present invention can solve the problem by a DNA aptamer which contains artificial nucleotides and binds to vWF.

1 Claim, 12 Drawing Sheets
Specification includes a Sequence Listing.

Fig. 1-1
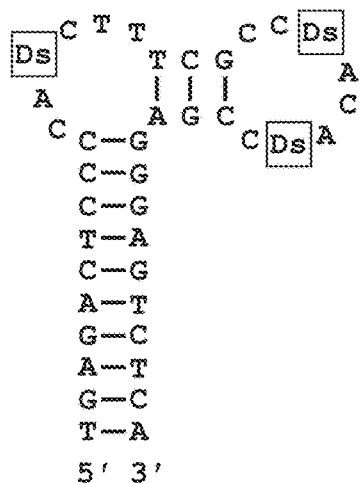
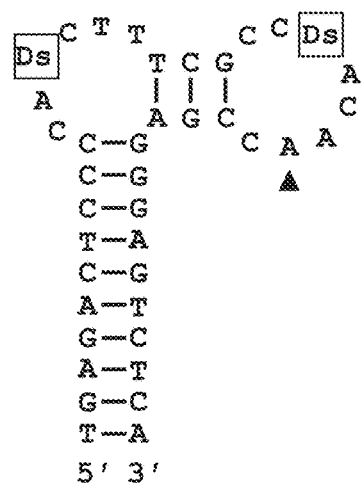
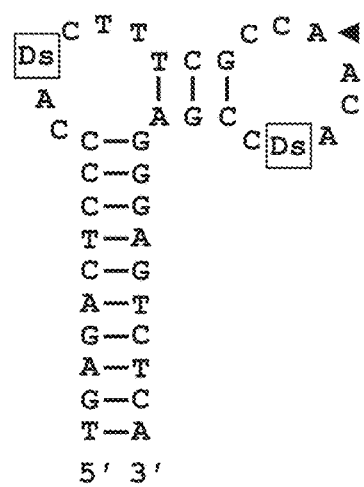
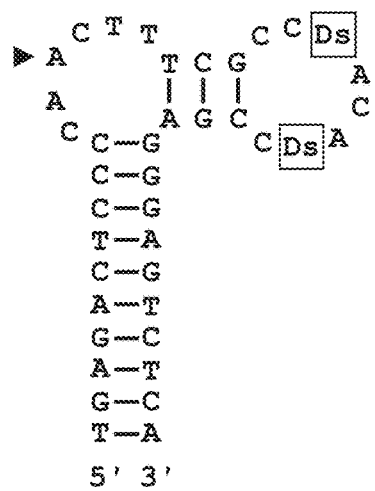
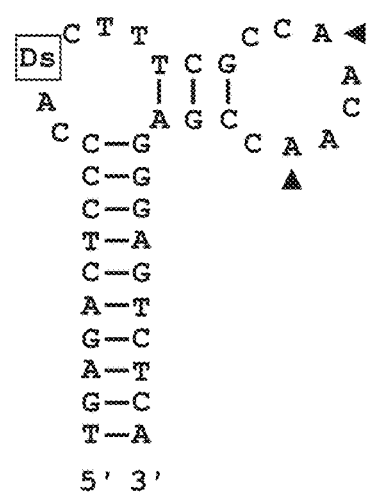

Fig. 2
A
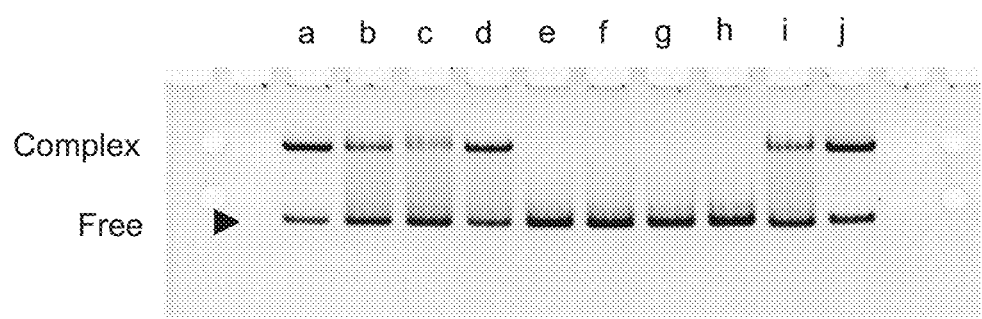
B
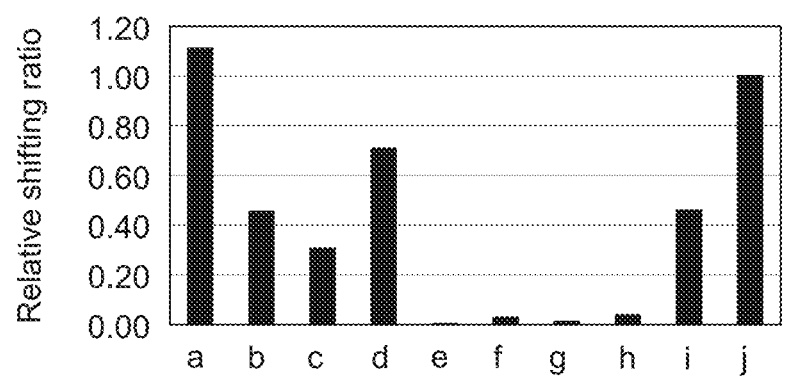

Fig. 6-1
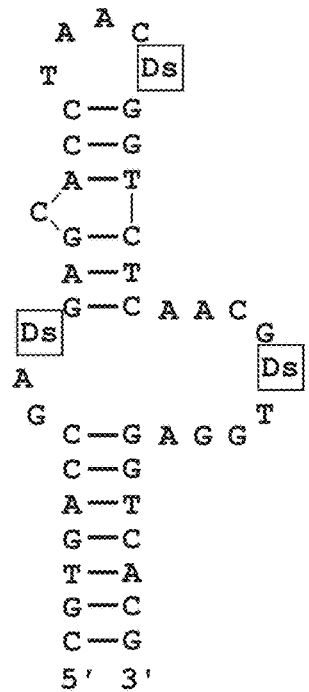
m vWF2-DsDsDs SEQ ID NO: 13
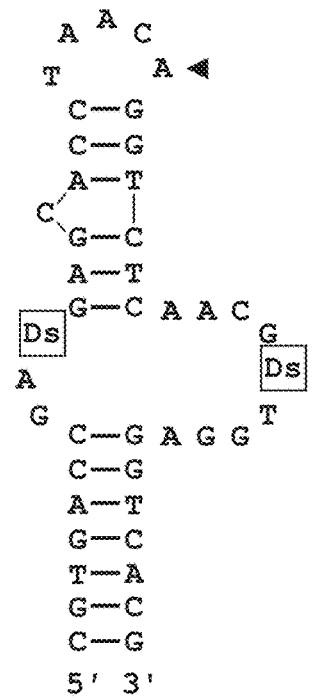
n vWF2-DsADs SEQ ID NO: 14
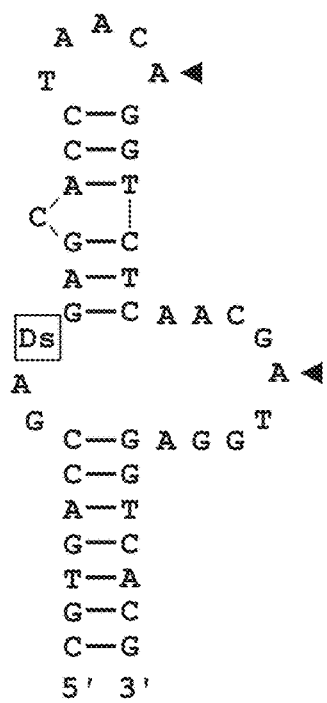
o vWF2-DsAA SEQ ID NO: 15
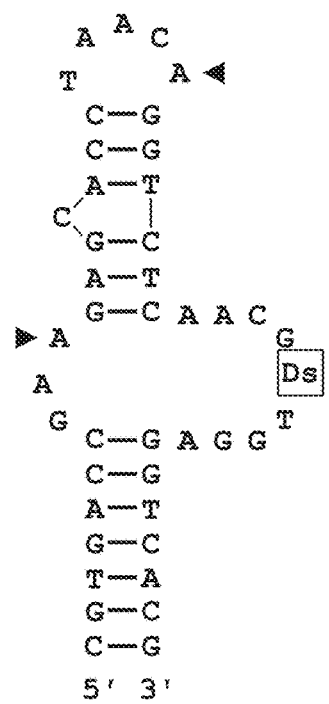
p vWF2-AADs SEQ ID NO: 16

Fig. 6-2
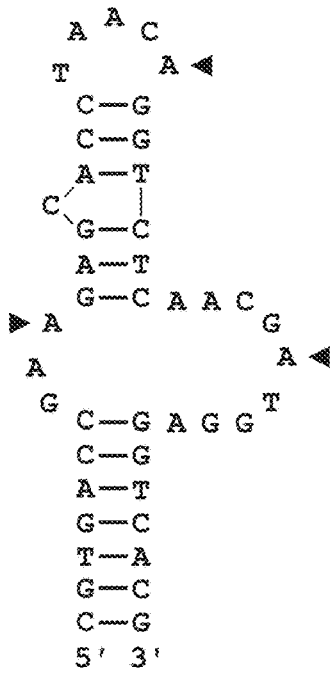
q vWF2-AAA
SEQ ID NO: 17
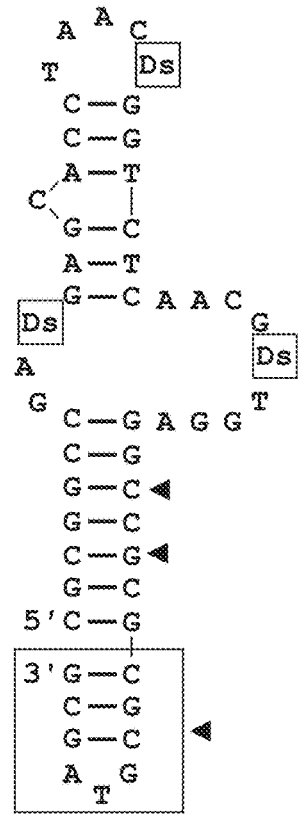
r vWF2-DsDsDs-mhGC
SEQ ID NO: 18
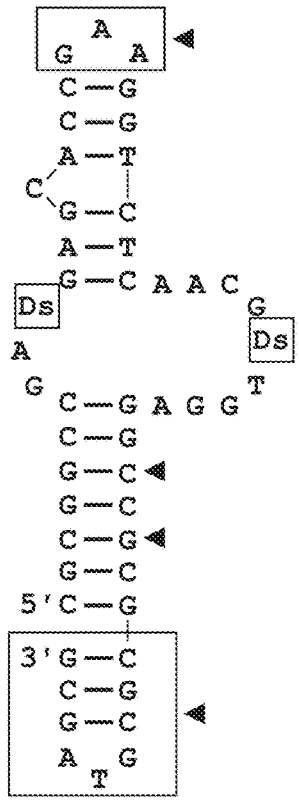
s vWF2-DsDsDs-2mhGC
SEQ ID NO: 21
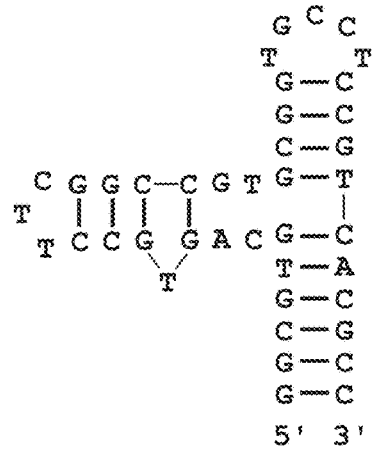
j ARC1172
SEQ ID NO: 10

DNA APTAMER THAT BINDS TO VWF

CROSS-REFERENCE TO RELATED APPLICATIONS

This application is a National Stage application of PCT/JP2016/081518, filed Oct. 25, 2016, which claims priority from Japanese application JP 2015-214848, filed Oct. 30, 2015.

TECHNICAL FIELD

The present invention relates to a DNA aptamer that binds to vWF comprising artificial nucleotide(s), a pharmaceutical composition comprising the DNA aptamer, and a method for detecting vWF using the DNA aptamer.

BACKGROUND ART

A nucleic acid fragment having binding activity to a target molecule is referred to as a "nucleic acid aptamer," and extensive applications thereof as nucleic acid pharmaceuticals to medical practice have been expected. A nucleic acid aptamer can be prepared via in vitro selection (the SELEX technique) by selecting and isolating a nucleic acid fragment that binds to a target molecule from a library of nucleic acid fragments comprising random nucleotide sequences.

vWF is a blood coagulation factor existing in the blood, and it is known that genetic mutation thereof is involved in the von Willebrand's disease and the like, and that acquired thrombotic thrombocytopenic purpura and the like are induced upon production of an autoantibody to vWF. In the past, several nucleic acid aptamers binding to vWF have been developed (Non-Patent Literature 1 and Non-Patent Literature 2). In comparison with an antibody, which is a protein composed of 20 amino acid species, a conventional nucleic acid aptamer is composed of 4 types of bases only, and variations thereof are limited. Accordingly, properties such as a binding ability, a dissociation rate, stability, and the like were not sufficient. Therefore, it was important to improve such properties, in order to use a nucleic acid aptamer in the medical field including treatment and diagnosis.

CITATION LIST

Non-Patent Literature

Non-Patent Literature 1: Sadler, J. E., 1998, Annu. Rev. Biochem., 67, pp. 395-424
Non-Patent Literature 2: Gilbert, J. C. et al, 2007, Circulation, 116, pp. 2678-2686

SUMMARY OF INVENTION

Technical Problem

Accordingly, development of an aptamer binding to vWF, which exhibits a binding ability, a dissociation rate, and/or stability superior to those of a conventional nucleic acid aptamer is needed.

Solution to Problem

The present inventors obtained a DNA aptamer comprising artificial nucleotide(s) that firmly binds to vWF by conducting 2 types of SELEX techniques (i.e., the predetermined method and the random library method described in WO 2013/073602) against vWF utilizing artificial base pairing developed by them. They also have conducted further studies concerning the obtained DNA aptamer and, as a consequence, discovered that such DNA aptamer exhibited a binding ability superior to that of a conventional nucleic acid aptamer (ARC1172) in terms of $K_D$ and/or $k_{off}$ (e.g., 10 times or lower $K_D$ and/or $k_{off}$). Also, the obtained DNA aptamer was found to exhibit high Tm value and/or excellent nuclease resistance.

The present invention is based on such finding and encompasses the following aspects.

(1) A DNA aptamer that binds to a vWF protein comprising the nucleotide sequence (i) or (ii) below:

(i) the nucleotide sequence as shown in any of SEQ ID NOs: 13 to 16, 19, and 20; or (ii) a nucleotide sequence in which one or several nucleotides are added, deleted, and/or substituted in the nucleotide sequence (i) at position(s) other than that of 7-(2-thienyl)-3H-imidazo[4,5-b]pyridin-3-yl.

(2) The DNA aptamer according to (1), wherein the nucleotide sequence (i) is a sequence as shown in SEQ ID NO: 13, 14, 19, or 20.

(3) The DNA aptamer according to (1) or (2), which comprises 1 to 5 GC pairs at the terminus of the nucleotide sequence.

(4) The DNA aptamer according to any of (1) to (3), which further comprises a mini-hairpin structure at the 3'-terminus of the nucleotide sequence, wherein the mini-hairpin structure is composed of the nucleic acid regions (A) to (C) sequentially ligated from the 5'-terminus toward the 3'-terminus:

(A) a first nucleic acid region consisting of 2 to 5 arbitrary nucleotides:

(B) a second nucleic acid region consisting of a nucleotide sequence of GNA or GNNA (wherein each "N" represents any of G, T, A, or C); and (C) a third nucleic acid region consisting of a nucleotide sequence complementary to the first nucleic acid region, and wherein the first nucleic acid region and the third nucleic acid region form a stem portion by base pairing, and the second nucleic acid region forms a loop portion.

(5) A DNA aptamer that binds to a vWF protein comprising the nucleotide sequence (i) or (ii) below:

(i) the nucleotide sequence as shown in SEQ ID NO: 18 or 21; or (ii) a nucleotide sequence in which one or several nucleotides are added, deleted, and/or substituted in the nucleotide sequence (i) at position(s) other than that of 7-(2-thienyl)-3H-imidazo[4,5-b]pyridin-3-yl.

(6) The DNA aptamer that binds to a vWF protein comprising the nucleotide sequence according to any of (1) to (5).

(7) A DNA aptamer that binds to a vWF protein comprising the nucleotide sequence (I) or (II) below:

(I) the nucleotide sequence as shown in any of SEQ ID NOs: 1 to 4, 9, and 11; or (II) a nucleotide sequence in which one or several nucleotides are added, deleted, and/or substituted in the nucleotide sequence (I) at position(s) other than that of 7-(2-thienyl)-3H-imidazo[4,5-b]pyridin-3-yl.

(8) The DNA aptamer according to (7), wherein the nucleotide sequence (I) is a sequence as shown in SEQ ID NO: 1 or 11.

(9) The DNA aptamer according to (7) or (8), which comprises 1 to 5 GC pairs at the terminus of the nucleotide sequence.

(10) The DNA aptamer according to any of (7) to (9), which further comprises a mini-hairpin structure at the 3'-terminus of the nucleotide sequence, which further comprises a mini-hairpin structure at the 3'-terminus of the nucleotide sequence, wherein the mini-hairpin structure consists of the nucleic acid regions (A) to (C) sequentially ligated from the 5'-terminus toward the 3'-terminus:

(A) a first nucleic acid region consisting of 2 to 5 arbitrary nucleotides:

(B) a second nucleic acid region consisting of a nucleotide sequence of GNA or GNNA (wherein each "N" represents any of G, T, A, or C); and (C) a third nucleic acid region consisting of a nucleotide sequence complementary to the first nucleic acid region, and wherein the first nucleic acid region and the third nucleic acid region form a stem portion by base pairing, and the second nucleic acid region forms a loop portion.

(11) A DNA aptamer that binds to a vWF protein comprising the nucleotide sequence (I) or (II) below:

(I) the nucleotide sequence as shown in SEQ ID NO: 12; or (II) a nucleotide sequence in which one or several nucleotides are added, deleted, and/or substituted in the nucleotide sequence (I) at position(s) other than that of 7-(2-thienyl)-3H-imidazo[4,5-b]pyridin-3-yl.

(12) A DNA aptamer that binds to a vWF protein consisting of the nucleotide sequence according to any of (7) to (11).

(13) An agent for detecting a vWF protein comprising the DNA aptamer according to any of (1) to (12).

(14) A kit for detecting a vWF protein comprising the DNA aptamer according to any of (1) to (12).

(15) A pharmaceutical composition comprising the DNA aptamer according to any of (1) to (12).

(16) The pharmaceutical composition according to (15) for treatment and/or prevention of a disease selected from the group consisting of thrombosis, thrombotic thrombocytopenic purpura, intracranial embolism, brain embolism, carotid artery stenosis, thrombotic microangiopathy, and acute myocardial infarction.

(17) A method for detecting a vWF protein comprising:

a step of contacting a sample obtained from a subject with the DNA aptamer according to any one of claims 1 to 12; and a step of detecting a vWF protein based on the binding between the sample and the DNA aptamer.

This description includes the disclosure of Japanese Patent Application No. 2015-214848, to which present application claims priority.

Advantageous Effects of Invention

The present invention provides a DNA aptamer binding to vWF that has a binding ability, a dissociation rate, and/or stability superior to those of a conventional nucleic acid aptamer. Further, the DNA aptamer according to the present invention provides a method for detecting vWF, a method for assisting diagnosis of disease such as thrombosis, and a pharmaceutical composition used for treatment and/or prevention of a disease such as thrombosis.

BRIEF DESCRIPTION OF DRAWINGS

FIG. 1-2 shows the putative secondary structures of the DNA aptamers prepared in Example 3. On the basis of vWF1-DsDsDs (SEQ ID NO: 1), 5'-terminal Ds and 3'-terminal Ds were both substituted with A to prepare vWF1-ADsA (SEQ ID NO: 6) shown as "f," 5'-terminal Ds and internal Ds were each substituted with A to prepare vWF1-AADs (SEQ ID NO: 7) shown as "g," all Ds bases were each substituted with A to prepare vWF1-AAA (SEQ ID NO: 8) shown as "h," and 3'-terminal Ds was substituted with A and the AT pair was removed from the terminal stem region to prepare vWF1-R1Ds (SEQ ID NO: 9) shown as "i." As a positive control, an existing vWF-binding DNA aptamer (i.e., ARC1172; SEQ ID NO: 10) shown as "j" was also prepared. An artificial base (Ds) is boxed and a site at which Ds is substituted with A is shown by an arrow head.

FIG. 2 shows the results of gel shift assays of the DNA aptamers prepared in Example 3 for binding to the A1 domain of vWF protein. In FIG. 2A, DNA bands were detected with electrophoresis by SYBR Gold. In FIG. 2B, the shifting ratio (binding ratio) of each oligonucleotide is graphed as a relative shifting ratio, when the gel shifting ratio of ARC1172 is designated as 1.0 (i.e., shifting ratio means that the ratio of the complex band when the signal of all bands in a particular lane is designated as 100%). The binding reaction was carried out at 37° C. and electrophoresis was carried out at 4° C. The complex refers to the DNA aptamer bound to the vWF A1 domain, and the free refers to a free DNA aptamer. "a" to "j" show the results obtained with the use of the aptamers "a" to "j," respectively, shown in FIG. 1-1 and FIG. 1-2.

FIG. 6-1 shows the putative secondary structures of the DNA aptamers prepared in Example 8. On the basis of vWF2-DsDsDs (SEQ ID NO: 13) shown as "m," internal Ds was substituted with A to prepare vWF2-DsADs (SEQ ID NO: 14) shown as "n," internal Ds and 3'-terminal Ds were each substituted with A to prepare vWF2-DsAA (SEQ ID NO: 15) shown as "o," and 5'-terminal Ds and internal Ds were each substituted with A to prepare vWF2-AADs (SEQ ID NO: 16) shown as "p." Ds is boxed and a site at which Ds is substituted with A is shown by an arrow head.

FIG. 6-2 shows the putative secondary structures of the DNA aptamers prepared in Example 8. On the basis of vWF2-DsDsDs (SEQ ID NO: 13), all Ds bases were each substituted with A to prepare vWF2-AAA (SEQ ID NO: 17) shown as "q," the AT pairs in the stem region were substituted with GC pairs and mini-hairpin DNA was added to the 3' terminus to prepare vWF2-DsDsDs-mhGC (SEQ ID NO: 18) shown as "r," and the internal loop region of WF2-DsDsDs-mhGC (SEQ ID NO: 18) was substituted with the partial sequence of the loop (5'-GAA-3') of mini-hairpin DNA to prepare vWF2-DsDsDs-2mhGC (SEQ ID NO: 21) shown as "s." As a positive control, an existing vWF-binding DNA aptamer (i.e., ARC1172; SEQ ID NO: 10) shown as "j" was also prepared. Ds is boxed, a site at which Ds is substituted with A and a site at which the AT pairs are substituted with GC pairs are each shown by an arrow head, and a site to which a mini-hairpin structure is added and a site which is substituted with the loop region of the mini-hairpin DNA are each boxed with an arrow head.

DESCRIPTION OF EMBODIMENTS

1. Definition

Figure 1:
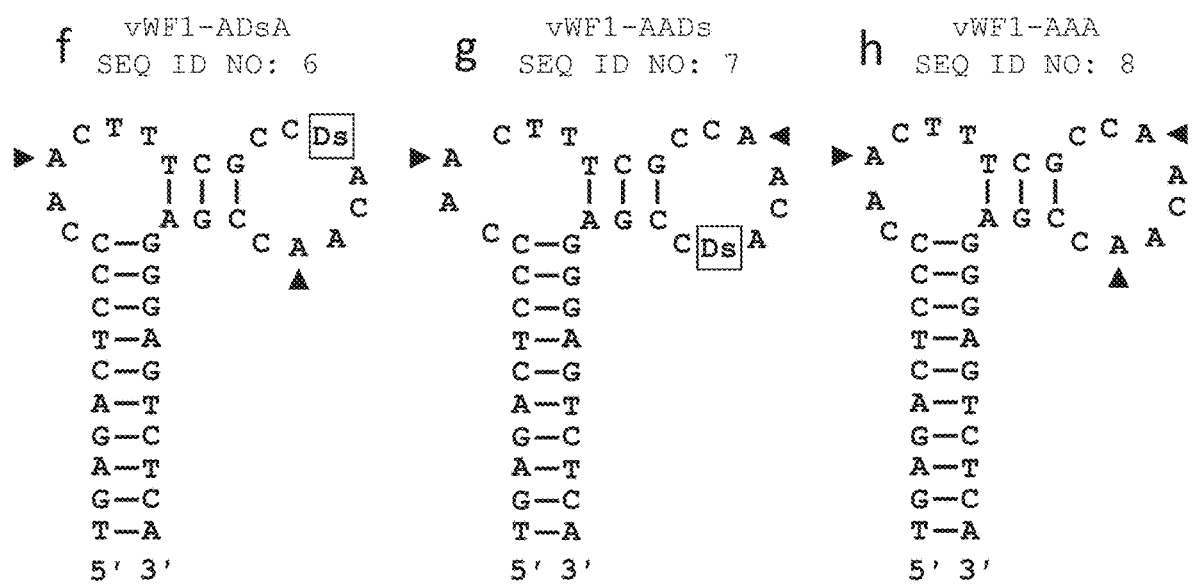
FIG. 1-1 shows the putative secondary structures of the DNA aptamers prepared in Example 3. On the basis of vWF1-DsDsDs (SEQ ID NO: 1) shown as "a," 3'-terminal Ds was substituted with A to prepare vWF1-DsDsA (SEQ ID NO: 2) shown as "b," internal Ds was substituted with A to prepare vWF1-DsADs (SEQ ID NO: 3) shown as "c," 5'-terminal Ds was substituted with A to prepare vWF1-ADsDs (SEQ ID NO: 4) shown as "d," and internal Ds and 3'-terminal Ds were each substituted with A to prepare vWF1-DsAA (SEQ ID NO: 5) shown as "e." An artificial base (Ds) is boxed and a site at which Ds is substituted with A is shown by an arrow head. In the figure, bold lines indicate bases capable of forming Watson-Crick base pairs, and solid lines indicate base linkage via phosphodiester bond. Bold lines and solid lines are used in the same manner in FIGS. 1-2, 3, 6-1, and 6-2 below.

Definitions of general terms used herein are described below.

The term "nucleic acid" or "nucleic acid molecule" used herein refers to, in principle, a biopolymer composing nucleotides as composing units ligated to each other via phosphodiester bond.

The term "natural nucleotide" used herein refers to a nucleotide that exists in nature. Examples thereof include DNA composed of deoxyribonucleotides comprising any natural bases selected from among adenine, guanine, cytosine, and thymine, RNA composed of ribonucleotides comprising any natural bases selected from among adenine, guanine, cytosine, and thymine, and a combination thereof.

The term "unnatural nucleotide" used herein refers to a nucleotide composed of artificial bases that does not exist in nature. Phosphoric acid groups and sugars constituting the unnatural nucleotide according to the present invention are structurally identical to the phosphoric acid groups and sugars constituting a natural nucleotide.

The term "artificial base" or "base analog" used herein refers to an artificially constructed chemical substance having properties similar to those of a natural base constituting a natural nucleotide. As with a natural base, it has a base analog which can form an artificial base pair therewith (hereafter, referred to as a "complementary artificial base"). The term "artificial base pairing" used herein refers to base pairing formed of a pair of complementary artificial bases, in the same way natural bases such as adenine and thymine, adenine and uracil, or guanine and cytosine. The term "artificial base pairing" encompasses chemical bonding via a hydrogen bond as observed in base pairing between natural bases, physical bonding via molecular structure-based interlocking between artificial bases, and stacking effects via hydrophobic interaction.

"Properties similar to those of natural bases" of an artificial base include properties capable of replication or transcription (including reverse transcription) of nucleic acids by complementarity caused by artificial base pairing. As with the case of natural bases, artificial bases have exclusive selectivity in artificial base pairing. In the presence of an unnatural nucleotide comprising a pair of complementary artificial bases in a substrate nucleotide, accordingly, a nucleic acid molecule comprising an unnatural nucleotide can also be accurately replicated or transcribed as with a natural nucleotide based on complementarity between artificial bases. In the presence of an unnatural nucleotide, accordingly, a DNA molecule can be amplified via nucleic acid amplification, such as PCR.

Specific examples of the artificial bases include 7-(2-thienyl)-3H-imidazo[4,5-b]pyridin-3-yl (referred to as "Ds" herein), 2-nitropyrrol-1-yl (referred to as "Pn" herein), 2-formyl-1H-pyrrol-1-yl (referred to as "Pa" herein), 2-amino-imidazo[1,2-a]-1,3,5-triazin-4(8H)-one (referred to as "P" herein), 6-amino-5-nitro-2(1H)-pyridone (referred to as "Z" herein), 6-methylisoquinoline-1(2H)-thione (referred to as "5SICS" herein), 3-methoxynaphthalen-2-yl (referred to as "NaM" herein), and 2-methoxy-4-methylphenyl (referred to as "MMO2" herein). Among these artificial bases, examples of complementary artificial bases of Ds include Pn and Pa, an example of a complementary artificial base of P is Z, and examples of complementary artificial bases of 5SICS include NaM and MMO2.

When a substrate does not comprise an unnatural nucleotide having complementary artificial base, at the time of replication or transcription, an artificial base can undergo alternative base pairing with a natural base having similar structure and/or property with the complementary artificial base. In such a case, an unnatural nucleotide in the template nucleic acid molecule will be substituted with a natural nucleotide after replication or transcription. For example, Ds is known to be substituted with A or T.

The term "modified base" used herein refers to an artificially and chemically modified base. Examples of modified bases include modified pyrimidine, such as 5-hydroxycytosine, 5-fluorouracil, 4-thiouracil, 5-(3-indole-2-ethyl)uracil, and 5-(4-hydroxyphenyl-2-ethyl)uracil), modified purine, such as 6-methyladenine and 6-thioguanosine, and other heterocyclic bases.

The term "DNA aptamer" used herein refers to an aptamer composed of DNAs. A DNA aptamer is a ligand molecule that firmly and specifically binds to a target molecule through a conformational structure formed based on a secondary and a tertiary structure of a single-stranded nucleic acid molecule via a hydrogen bond or other means. When a DNA aptamer has an ability of specifically inhibiting or suppressing functions such as physiological activity of a target molecule, such DNA aptamer can serve as a functional inhibitor of a target molecule. The term "functional inhibition of a target molecule" used herein refers to inhibition or suppression of biological functions, such as catalytic activity, function of gene expression regulation (including regulation of transcription, translation, and transportation), and regulation of apoptosis of a target molecule. The term "target molecule" used herein refers to a substance to which the DNA aptamer can bind. In the present invention, a target molecule is vWF.

The term "vWF" used herein refers to a von Willebrand factor protein (also referred to as a "vWF protein" herein). vWF is a blood coagulation factor existing in the blood, and it is known that genetic mutation thereof is involved in various diseases such as the von Willebrand's disease, and that acquired thrombotic thrombocytopenic purpura and the like are induced upon production of an autoantibody to vWF. In the present invention, organism species from which vWF protein is derived are not particularly limited. Examples thereof include mammals, for example, primates such as humans and chimpanzees, experimental animals such as rats and mice, livestock animals such as pigs, cows, horses, sheep, and goats, and pet animals such as dogs and cats, preferably, human vWF.

vWF comprises, for example, (a) the amino acid sequence as shown in SEQ ID NO: 28; (b) an amino acid sequence in which one or several amino acids are added, deleted, and/or substituted in the amino acid sequence as shown in SEQ ID NO: 28, or (c) an amino acid sequence having 70% or higher, 80% or higher, and preferably 90% or higher, 95% or higher, 97% or higher, 98% or higher, or 99% or higher identity to the amino acid sequence as shown in SEQ ID NO: 28. vWF may consist of any of such amino acid sequences. The degree of identity herein is determined with the use of software that computes the degree of identity among a plurality sequences (e.g., FASTA, DANASYS, or BLAST) with the default settings.

The term "vWF A1 domain" used herein refers to a domain in vWF having an ability to bind to a GPIb receptor on platelets. For example, the vWF A1 domain comprises (a) an amino acid sequence of positions 1238 to 1481 of SEQ ID NO: 28, (b) an amino acid sequence in which one or several amino acids are added, deleted, and/or substituted in the amino acid sequence of positions 1238 to 1481 of SEQ ID NO: 28, or (c) an amino acid sequence having 70% or higher, 80% or higher, and preferably 90% or higher, 95% or higher, 97% or higher, 98% or higher, or 99% or higher identity to the amino acid sequence of positions 1238 to 1481 of SEQ ID NO: 28. The vWF A1 domain may consist of any of such amino acid sequences.

The term "several" used herein refers to, for example, 1 to 6, 1 to 5, 1 to 4, 1 to 3, or 1 or 2.

The term "mini-hairpin structure" used herein refers to a structure comprising the 3 DNA nucleic acid regions described below: i.e., a first nucleic acid region, a second nucleic acid region, and a third nucleic acid region, sequentially ligated from the 5'-terminus toward the 3'-terminus. Mini-hairpin-shaped DNA may improve heat stability of the DNA aptamer by enhancing degradation resistance against a nuclease and/or increasing a Tm value of the DNA aptamer.

The "first nucleic acid region" is a nucleic acid region consisting of 2 to 5 arbitrary nucleotides. The nucleotide is a deoxyribonucleotide comprising a base selected from among guanine (G), adenine (A), cytosine (C), and thymine (T). A base constituting the nucleic acid region is preferably guanine or cytosine. This is because when the first nucleic acid region forms a stem structure with the third nucleic acid region described below, a Tm value elevates as the GC content increases, and the stem structure can be maintained stably. Accordingly, most preferably, the full-length nucleotide sequence of the first nucleic acid region is composed of G and/or C.

The "second nucleic acid region" is a nucleic acid region consisting of a nucleotide sequence 5'-GNA-3' or 5'-GNNA-3'. In the sequence, each "N" is a natural base (G, A. T. or C) such as T.

The "third nucleic acid region" is a nucleic acid region consisting of a nucleotide sequence complementary to the first nucleic acid region. Accordingly, the nucleotide sequence of the third nucleic acid region is determined based on the nucleotide sequence of the first nucleic acid region, and the first nucleic acid region forms base pairing with the third nucleic acid region in the molecule. As a result, the first nucleic acid region and the third nucleic acid region form a completely base-paired stem structure, and the second nucleic acid region flanked by the first nucleic acid region and the third nucleic acid region forms loop structures therewith, and, as a whole, mini-hairpin-shaped DNA consisting of 7 to 14 nucleotides is formed. An example of mini-hairpin-shaped DNA is DNA consisting of a nucleotide sequence CGCGTAGCG (SEQ ID NO: 26).

2. DNA Aptamer that Binds to vWF

In one aspect, the present invention relates to a DNA aptamer that binds to vWF comprising the nucleotide sequence (i) or (ii) below:

(i) the nucleotide sequence as shown in any of SEQ ID NOs: 13 to 16, 19, and 20, preferably, the nucleotide sequence as shown in any of SEQ ID NO: 13, 14, 19, and 20; or (ii) a nucleotide sequence in which one or several nucleotides are added, deleted, and/or substituted in the nucleotide sequence (i) at position(s) other than that of Ds.

In one embodiment, the nucleotide sequence (i) comprises, at its terminus, base pair(s), for example, 1 to 5, 1 to 4, 1 to 3, 1 or 2, or 1 GC pair(s). Base pair(s) at the terminus may increase the Tm value and enhance thermal stability of the DNA aptamer. In addition to or instead of the base pair(s) mentioned above, the nucleotide sequence (i) may comprise a sequence constituting a mini-hairpin structure at, for example, the 3'-terminus (hereafter, also referred to as the "mini-hairpin sequence").

Examples of sequences in which the mini-hairpin sequence is added to the sequence (i) include the sequence as shown in SEQ ID NO: 18 in which the mini-hairpin sequence is added to the sequence as shown in SEQ ID NO: 19, and the sequence as shown in SEQ ID NO: 21 in which the mini-hairpin sequence is added to the sequence as shown in SEQ ID NO: 20.

In one aspect, the present invention relates to a DNA aptamer that binds to vWF comprising the nucleotide sequence as shown in SEQ ID NO: 18 or 21 or a nucleotide sequence in which one or several nucleotides are added, deleted, and/or substituted in to the nucleotide sequence as shown in SEQ ID NO: 18 or 21 at position(s) other than that of Ds.

In one embodiment, the DNA aptamer according to the present invention comprises the nucleotide sequence (i) or (ii) or a nucleotide sequence in which base pair(s) and/or a mini-hairpin sequence is added thereto at the terminus.

The DNA aptamer according to the present invention comprising the nucleotide sequence (i) or (ii) binds to vWF, for example, the vWF A1 domain.

The DNA aptamer according to the present invention comprising the nucleotide sequence (i) or (ii) can have a high vWF-binding ability in terms of the dissociation constant ($K_D$) and/or the dissociation rate ($k_{off}$). Here, $K_D$ is a dissociation constant represented by $k_{off}$ (dissociation rate)/$k_{on}$ (binding rate). As the $K_D$ value decreases, affinity to the target becomes higher. As the $k_{off}$ value decreases the DNA aptamer is less likely to dissociate after it binds to the target.

The DNA aptamer according to the present invention comprising the nucleotide sequence (i) or (ii) can have $K_D$ of $1.0\times10^{-7}$ or lower, $1.0\times10^{-8}$ or lower, or $1.0\times10^{-9}$ or lower, and preferably $5.0\times10^{-10}$ or lower, $3.0\times10^{-10}$ or lower, $1.0\times10^{-10}$ or lower, or $8.0\times10^{-11}$ M or lower, in vWF-binding analysis using Biacore.

The DNA aptamer according to the present invention comprising the nucleotide sequence (i) or (ii) can have $k_{off}$ of $1.0\times10^{-1}$ or lower, and preferably $9.0\times10^{-2}$ or lower, $8.0\times10^{-2}$ or lower, $7.0\times10^{-2}$ or lower, $6.0\times10^{-2}$ or lower, or $5.0\times10^{-2}$ (1/Ms) or lower, in vWF-binding analysis using Biacore.

In one aspect, the present invention relates to a DNA aptamer that binds to vWF comprising the nucleotide sequence (I) or (II) below:

(I) the nucleotide sequence as shown in any of SEQ ID NOs: 1 to 4, 9, and 11, preferably, the nucleotide sequence as shown in SEQ ID NO: 1 or 11; or (II) a nucleotide sequence in which one or several nucleotides are added, deleted, and/or substituted in the nucleotide sequence (I) at position(s) other than that of Ds.

In one embodiment, the nucleotide sequence (i) comprises, at its terminus, base pair(s), for example, 1 to 5, 1 to 4, 1 to 3, 1 or 2, or 1 GC pair(s). Base pairs at the terminus may increase the Tm value and enhance heat stability of the DNA aptamer. In addition to or instead of the base pair(s) mentioned above, the nucleotide sequence (I) may comprise a mini-hairpin sequence at, for example, the 3'-terminus.

An example of a sequence in which the mini-hairpin sequence is added to the sequence (I) includes the sequence as shown in SEQ ID NO: 12 in which the mini-hairpin sequence is added to the sequence as shown in SEQ ID NO: 11.

Accordingly, in one aspect, the present invention relates to a DNA aptamer that binds to vWF comprising the nucleotide sequence as shown in SEQ ID NO: 12 or a nucleotide sequence in which one or several nucleotides are added, deleted, substituted, and/or inserted in the nucleotide sequence as shown in SEQ ID NO: 12 at position(s) other than that of Ds.

In one embodiment, the DNA aptamer according to the present invention comprises the nucleotide sequence (I) or (II) or a nucleotide sequence in which base pair(s) and/or a mini-hairpin sequence is added at the terminus.

The DNA aptamer according to the present invention comprising the nucleotide sequence (I) or (II) binds to vWF, for example, vWF A1 domain.

The DNA aptamer according to the present invention comprising the nucleotide sequence (I) or (II) can have an excellent vWF-binding ability, especially in the dissociation rate ($k_{off}$). For example, the DNA aptamer according to the present invention comprising the nucleotide sequence (I) or (II) can have $k_{off}$ of $1.0\times10^{-1}$ or lower, $1.0\times10^{-2}$ or lower, and preferably $5.0\times10^{-3}$ or lower, $4.0\times10^{-3}$ or lower, $3.0\times10^{-3}$ or lower, or $2.0\times10^{-3}$ or lower (1/Ms), in vWF-binding analysis using Biacore.

Also, the DNA aptamer according to the present invention comprising the nucleotide sequence (I) or (II) can have $K_D$ of $1.0\times10^{-6}$ or lower, $1.0\times10^{-7}$ or lower, $1.0\times10^{-8}$ or lower, and preferably $5.0\times10^{-9}$ or lower, $4.0\times10^{-9}$ or lower, $3.0\times10^{-9}$ or lower, or $2.0\times10^{-9}$ M or lower, in vWF-binding analysis using Biacore.

The length of the DNA aptamer comprising the sequence (i) or (ii) or the sequence (I) or (II) (hereafter, simply referred to as the "DNA aptamer according to the present invention") is, for example, 150 mer or shorter, 140 mer or shorter, 130 mer or shorter, 120 mer or shorter, or 110 mer or shorter, and preferably 100 mer or shorter, 90 mer or shorter, 80 mer or shorter, 70 mer or shorter, 60 mer or shorter, or 50 mer or shorter.

The DNA aptamer according to the present invention may arbitrarily comprise a base analog, another artificial base, another modified base, or the like, in addition to Ds.

The DNA aptamer according to the present invention may be modified with the addition of other substances, such as polyethylene glycol (PEG) (e.g., a PEG polymer of about 20 to 60 kDa), an amino acid, a peptide, inverted dT, a lipid, a dye, a fluorescent substance, an enzyme, a radioactive substance, and biotin. Such substance may be linked via a known linker, if needed. Examples of linkers that can be used herein include a nucleotide linker, a peptide linker, and a linker containing a disulfide bond. It is generally known that a half-life of the DNA aptamer is extended by conjugating PEG to the DNA aptamer.

A method for producing the DNA aptamer according to the present invention is not particularly limited. A method known in the art may be employed. For example, the DNA aptamer according to the present invention can be chemically synthesized based on the sequences indicated above in accordance with a known solid-phase synthesis method. Regarding a method of chemical synthesis of nucleic acids, see, for example, Current Protocols in Nucleic Acid Chemistry, Volume 1, Section 3. Many life science manufacturers (e.g., Takara Bio Inc. and Sigma-Aldrich Corporation) provide contract manufacturing services concerning such chemical synthesis, and such services may be used. A DNA aptamer may be prepared by synthesizing several fragments based on the DNA aptamer sequence and then ligating the fragments via, for example, intramolecular annealing or ligation by a ligase.

The DNA aptamer according to the present invention prepared via chemical synthesis is preferably purified by a method known in the art before use. Examples of methods of purification include gel purification, affinity column purification, and HPLC.

3. Pharmaceutical Composition Comprising DNA Aptamer

In one aspect, the present invention relates to a pharmaceutical composition comprising the DNA aptamer according to the present invention. The pharmaceutical composition according to the present invention can comprise one or more other drugs, provided that the binding ability of the DNA aptamer according to the present invention to vWF is not lost.

In one embodiment, the present invention relates to a pharmaceutical composition comprising the DNA aptamer and another drug for delivering the drug. The other drugs may be bound to the DNA aptamer, so that the drug can be efficiently delivered to the lesion, utilizing the ability of the DNA aptamer to bind to vWF. A method for binding the DNA aptamer to the drug is not particularly limited.

Target diseases to be prevented and/or treated with the pharmaceutical composition according to the present invention are diseases that can be caused by, for example, mutation or overexpression of the vWF gene and production of an autoantibody to vWF (such disease may be referred to as the "vWF-associated disease" hereinbelow). Examples of vWF-associated diseases include thrombosis, thrombotic thrombocytopenic purpura, intracranial embolism, brain embolism, carotid artery stenosis, thrombotic microangiopathy, and acute myocardial infarction.

Therapeutic effects are expected by administrating the pharmaceutical composition to a subject afflicted with such disease, and preventive effects are expected by administrating the pharmaceutical composition to a subject at risk of such disease.

The pharmaceutical composition according to the present invention can comprise a pharmaceutically acceptable carrier. The term "pharmaceutically acceptable carrier" refers to a substance generally used in the art that facilitates preparation of a pharmaceutical composition or application thereof to an organism, and such substance is added to the pharmaceutical composition in an amount that does not inhibit or suppress the activity of the pharmaceutical composition. Examples of carriers include an excipient, a binder, a disintegrator, a filler, an emulsifier, a fluidity adjustor, a lubricant, and a stabilizer.

Examples of "excipient" include a sugar, such as monosaccharide, disaccharide, cyclodextrin, and a polysaccharide (specific examples include, but are not limited to, glucose, sucrose, lactose, raffinose, mannitol, sorbitol, inositol, dextrin, maltodextrin, starch, and cellulose), metal salt (e.g., sodium phosphate, calcium phosphate, calcium sulfate, and magnesium sulfate), citric acid, tartaric acid, glycine, low-, middle-, and high-molecular-weight polyethylene glycol (PEG), Pluronic, and a combination thereof.

Examples of "binder" include starch glue using corn, wheat, rice, or potato starch, gelatin, gum tragacanth, methylcellulose, hydroxypropyl methylcellulose, carboxymethyl cellulose sodium, and polyvinyl pyrrolidone.

Examples of "disintegrator" include the starch, carboxymethylstarch, crosslinked polyvinyl pyrrolidone, agar, alginic acid, sodium alginate, and a salt thereof.

Examples of "filler" include the sugar and calcium phosphate (e.g., tricalcium phosphate and calcium hydrogen phosphate).

Examples of "emulsifier" include sorbitan fatty acid ester, glycerin fatty acid ester, sucrose fatty acid ester, and propylene glycol fatty acid ester.

Examples of "fluidity adjuster" and "lubricant" include silicate, talc, stearate, and polyethylene glycol.

Examples of "stabilizer" include an anti-oxidant, such as ascorbic acid or sulfite, and sugar, such as trehalose or glucose.

Such carrier may adequately be used, if needed. In addition to the additives described above, the pharmaceutical composition according to the present invention can comprise a corrigent, a solubilizer (a solubilizing agent), a suspension, a diluent, a surfactant, an absorbefacient (e.g., a quaternary ammonium salt and sodium lauryl sulfate), an extender, a wetting agent, a moisturizing agent (e.g., glycerin and starch), an absorbent (e.g., starch, lactose, kaolin, bentonite, and colloidal silicic acid), a disintegrator (e.g., saccharose, stearin, cacao butter, and hydrogenated oil), a coating agent, a colorant, a preservative, a flavoring agent, an aromatic agent, a sweetening agent, a buffer, an isotonizing agent, a soothing agent, solubilizer, or the like.

Examples of "surfactant" include alkali metal salt, alkaline earth metal salt, and ammonium salt of lignosulfonic acid, naphthalenesulfonic acid, phenolsulfonic acid, and dibutylnaphthalenesulfonic acid, alkyl aryl sulfonate, alkyl sulfate, alkyl sulfonate, fatty alcohol sulfate, fatty acid, sulfated fatty alcohol glycol ether, a condensate of a naphthalene sulfonate or naphthalene derivative and formaldehyde, a condensate of naphthalene, naphthalane sulfonic acid, or phenol and formaldehyde, polyoxyethylene octyl phenyl ether, ethoxylated isooctyl phenol, octyl phenol, nonyl phenol, alkylphenyl polyglycol ether, tributylphenyl polyglycol ether, tristearyl phenyl polyglycol ether, alkyl aryl polyether alcohol, a condensate of an alcohol/fatty alcohol and ethylene oxide, ethoxylated castor oil, polyoxyethylene alkyl ether, ethoxylated polyoxypropylene, lauryl alcohol polyglycol ether acetal, sorbitol ester, lignosulfite waste liquor, and methylcellulose.

A pharmaceutical composition according to this embodiment can contain 1 or more of the carriers mentioned above.

A dosage form of the pharmaceutical composition according to the present invention is not particularly limited, provided that an active ingredient is not inactivated and pharmacological effects can be exerted in vivo after administration. In general, a dosage form varies depending on a route of administration and/or prescription conditions.

Examples of dosage forms suitable for oral administration include solid preparations (including tablets, pills, sublingual formulations, capsules, drops, and troches), granules, powders, and liquids. If needed, solid preparations can be preparations with coating materials known in the art, such as sugar-coated tablets, gelatin-coated tablets, enteric coated tablets, film-coated tablets, double-layer tablets, or multi-layer tablets.

Parenteral administration is classified as systemic administration or topical administration, and topical administration is further classified as interstitial administration, transdermal administration, transmucosal administration, or transrectal administration. The pharmaceutical composition can be prepared in a dosage form suitable for the route of administration. Examples of dosage forms suitable for systemic or interstitial administration include injection preparations, which are liquids. Examples of dosage forms suitable for transdermal or transmucosal administration include liquids (including embrocation, eye drops, nasal drops, and inhalants), suspensions (including emulsifiers and cream agents), powders (including nasal drops and inhalants, pastes, gels, ointments, and plasters). An example of a dosage form suitable for transrectal administration is a suppository.

Specific configurations and sizes of the dosage forms mentioned above are not particularly limited, provided that they are within the scope of the dosage forms known in the art.

In principle, the pharmaceutical composition according to the present invention may be prepared in accordance with a method known in the art. For example, see the method described in Remington's Pharmaceutical Sciences (Merck Publishing Co., Easton, Pa.).

For example, injection preparations can be prepared by a method generally used in the art, comprising dissolving the DNA aptamer according to the present invention in a pharmaceutically acceptable solvent and adding a pharmaceutically acceptable carrier thereto, if needed.

Examples of "pharmaceutically acceptable solvent" include water, ethanol, propylene glycol, ethoxylated isostearyl alcohol, polyoxylated isostearyl alcohol, and a polyoxyethylene sorbitan fatty acid ester. Such solvent is preferably made isotonic to the blood, if needed.

The pharmaceutical composition according to the present invention can be administered to an organism in a pharmaceutically effective amount for treatment or prevention of a target disease such as cancer. A target organism is a vertebrate, preferably a mammal, and more preferably a human.

The pharmaceutical composition according to the present invention may be administered systemically or topically. An adequate administration route can be selected depending on a disease type, a site of disease onset, a stage, or the like. In the case of a disease that develops in a topical site, for example, topical administration directly to the site of disease onset and a region in the vicinity thereof by means of injection is preferable. This is because a sufficient amount of the DNA aptamer according to the present invention can be administered to a site to be treated (i.e., the tissue or organ) and other tissue is less likely to be affected. When the site to be treated cannot be identified or a disease develops throughout the body, systemic administration via intravenous injection or the like is preferable, although the administration route is not limited. By spreading the DNA aptamer according to the present invention through the blood flow throughout the body, it can be administered to a lesion that cannot be identified by diagnosis.

The pharmaceutical composition according to the present invention can be administered by any adequate method, provided that active ingredients are not inactivated. For example, a parenteral route (e.g., by means of injection, aerosol, topical application, instillation, or nasal drip) or an oral route may be employed, preferably, by injection.

In the case of injection administration, the site of injection is not particularly limited, provided that the DNA aptamer as an active ingredient is binding ability to a target substance. For example, intravenous, intraarterial, intrahepatic, intramuscular, intraarticular, intramedullary, intraspinal, intraventricular, transpulmonary, percutaneous, subcutaneous, intracutaneous, or intraperitoneal administration may be performed.

4. Method of Treatment and/or Prevention Using DNA Aptamer

In one aspect, the present invention relates to a method of treatment and/or prevention of a disease comprising administering the DNA aptamer or pharmaceutical composition according to the present invention to a subject.

An example of a disease to be prevented and/or treated with the pharmaceutical composition according to the present invention is the vWF-associated disease. Examples thereof include thrombosis, thrombotic thrombocytopenic purpura, intracranial embolism, brain embolism, carotid artery stenosis, thrombotic microangiopathy, and acute myocardial infarction.

Examples of animal species encompassed by "subjects" herein include mammals, and specific examples include primates such as humans and chimpanzees, experimental animals such as rats and mice, livestock animals such as pigs, cows, horses, sheeps, and goats, and pet animals such as dogs and cats, preferably, humans.

5. Detection Agent Comprising DNA Aptamer

In one aspect, the present invention relates to an agent for detecting vWF comprising the DNA aptamer according to the present invention. The agent for detecting vWF according to the present invention is an agent that is used for detecting vWF in vivo or in vitro utilizing the ability of the DNA aptamer according to the present invention to bind to vWF. For example, the DNA aptamer is labeled with a fluorescence reagent beforehand, and the labeled DNA aptamer is administered to an organism, so as to determine expression intensity of vWF in vivo and investigate localization thereof. This can assist diagnosis of the vWF-related diseases described above. The DNA aptamer according to the present invention is useful for imaging and tissue staining.

In one aspect, the present invention relates to a composition for detecting vWF comprising the DNA aptamer according to the present invention. The constitution of the composition is the same as described with regard to the pharmaceutical composition above and explanation thereof is accordingly omitted herein.

In one aspect, the present invention relates to a kit for detecting vWF comprising the DNA aptamer according to the present invention. In addition to the DNA aptamer according to the present invention, the kit according to the present invention may comprise, for example, a buffer, a label reagent, and/or instructions.

6. Method of vWF Detection

In one aspect, the present invention relates to a method for detecting vWF. The method comprises a step of contacting a sample obtained from a subject with the DNA aptamer according to the present invention and a step of detecting vWF based on the binding between the sample and the DNA aptamer. This method can assist diagnosis of the vWF-associated disease.

Samples used in the method of the present invention include tissue and biological samples. Tissue examples include sites of lesions, such as the brain, the heart, the liver, the pancreas, the lung, the bone marrow, the lymph node, and the spleen. For example, biopsy samples of such tissues can be used. Examples of biological samples include the blood, the blood plasma, the lymph, the interstitial fluid, the urine, and cells, such as peripheral blood cells, hair matrix cells, oral cavity cells, nasal cavity cells, intestinal tract cells, intravaginal cells, mucosal cells, and sputum (that can contain alveolar cells or tracheal cells), preferably, blood or blood plasma.

A step of detection in the method of detection according to the present invention is not particularly limited, provided that the binding between the sample and the DNA aptamer is utilized, and any known method may be employed. For example, SPR method, turbidimetric method, colorimetric method, or fluorescence method may be employed.

Surface plasmon resonance (SPR) is a phenomenon that the intensity of a reflected light decreases sharply at a particular angle of incidence (i.e., an angle of resonance) when a laser beam is irradiated to a metal thin film SPR is a measurement method based on the phenomenon described above and is capable of assaying a substance adsorbed on the surface of the metal thin film, which is a sensor, with high sensitivity. According to the present invention, for example, the target substance in the sample can then be detected by immobilizing the DNA aptamer according to the present invention on the surface of the metal thin film beforehand, allowing the sample to pass through the surface of the metal thin film, and detecting the difference of the amount of the substance adsorbed on the surface of the metal thin film resulting from the binding of the nucleic acid and target substance, between before and after the sample passes therethrough. Examples of known SPR techniques include the displacement method and the indirect competitive method, and any method may be employed herein.

Turbidimetry is a method comprising irradiating a light to a solution, optically assaying an attenuation in the light scattered by substances suspended in the solution or a light transmitted through the solution using a colorimeter or the like, and assaying the amount of the substance of interest in the solution. According to the present invention, the target substance in the sample can be quantitatively detected by assaying the absorbance before and after the DNA aptamer according to the present invention is added to the sample.

Also, the target substance can be detected by using an antibody reacting with the target substance in combination. For example, sandwich ELISA may be employed. With this technique, the DNA aptamer according to the present invention is first immobilized on a solid-phase support, the sample is added, and the target substance in the sample is then allowed to bind to the DNA aptamer. Subsequently, the sample is washed away, and the anti-target substance antibody is added and allowed to bind to the target substance. After washing, an adequately labeled secondary antibody is used to detect the anti-target substance antibody, and the target substance in the sample can be thus detected. Examples of solid-phase supports that can be used include insoluble supports in the form of beads, microplates, test tubes, sticks, test pieces, and the like, made of materials such as polystyrene, polycarbonate, polyvinyl toluene, polypropylene, polyethylene, polyvinyl chloride, nylon, polymethacryate, latex, gelatin, agarose, cellulose, sepharose, glass, metal, ceramic, or magnet.

In one aspect, the present invention relates to a method of assisting diagnosis as to whether or not a subject is afflicted with the vWF-associated disease. This method comprises: a step of administering the DNA aptamer according to the present invention or the agent for detecting vWF or composition for detecting vWF according to the present invention to a subject; and a step of detecting the DNA aptamer. When the DNA aptamer is detected at high concentration at a particular site in an organism, for example, it can be determined that the disease has developed at the site of interest. The step of detection may be carried out in accordance with a conventional technique. For example, the fluorescence method mentioned above may be employed.

EXAMPLES

Example 1: Selection of DNA Aptamer that Binds to vWF Using Ds-Predetermined DNA Library In accordance with the predetermined method described in WO 2013/073602, a DNA library comprising artificial bases (Ds) was prepared. The library used in the predetermined method was designed to comprise artificial bases (Ds) at particular fixed positions in a random nucleotide sequence. Briefly, a pool of DNA fragment (the total number of molecular species: 300 pmol, about $2 \times 10^{14}$ molecules) was used as the first-round library, the target protein (i.e., the vWF A1 domain. V003, U-Protein) was mixed, a pool of DNA that binds to the target protein was selected and isolated using magnetic beads, then the DNA-vWF A1 domain complex was cleaved via polyacrylamide gel electrophoresis to select and isolate the DNA of interest, and the resultant was amplified via PCR. In total, 8 rounds of selection procedures were performed. Table 1 shows the selection conditions. After the completion of the 8th round of selection, sequence analysis was performed, and the sequences of the DNA aptamers comprising artificial base(s) (Ds) were obtained.

TABLE 1

| | | | | | Selection conditions | | | | |
| --- | --- | --- | --- | --- | --- | --- | --- | --- | --- |
| | | DNA | Protein | Volume | Number of washing | | Gel | Electrophoresis | PCR |
| Round | Method | (nM) | (nM) | (ml) | Without urea | With 3M urea | conditions | conditions | cycles |
| 1 | a | 50 | 25 | 6 | 5 | — | — | — | 25 |
| 2 | a | 25 | 10 | 2 | 5 | — | — | — | 23 |
| 3 | b | 500 | 2000 | 0.05 | — | — | Native | 0.5× TBE, 4° C., 300 V, 40 min | 12 |
| 4 | b | 250 | 250 | 0.02 | — | — | Native | 0.5× TBE, 4° C., 300 V, 40 min | 16 |
| 5 | b | 125 | 125 | 0.04 | — | — | Native | 0.5× TBE, 4° C., 300 V, 40 min | 16 |
| 6 | a | 1 | 1 | 3 | 5 | — | — | — | 25 |
| 7 | a | 1 | 1 | 3 | 3 | 2 | — | — | 17 |
| 8 | b | 100 | 100 | 50 | — | — | +3M urea | 0.5× TBE, 4° C., 300 V, 40 min | 16 |

Method a: Complex biotinylation
Method b: Gel shift separation

As a result of sequencing the DNA library after the 8th round, 420,526 sequences for analysis were obtained. In accordance with the method of analysis described in WO 2013/073602, sequences that were deduced to retain artificial bases were extracted from among 100 or more clone sequences. As a result, 406,086 sequences were extracted in total. The number of sequences was counted, and the most common sequences were found to be single-copy sequences, which accounted for 80% or more of the whole, and 90% of the whole when similar sequences were included.

Example 2: Determination of DNA Aptamer Sequence

The following procedure was carried out in order to accurately identify the positions of artificial bases (Ds) and the accurate sequence was determined.

A probe sequence of a DNA fragment consisting of 25 bases that was designed to be specific to the most common sequence obtained in Example 1 was used (5'-ACTC-CCTCGGTTGTTGGCGAAAGTTG-3': SEQ ID NO: 22). The 5'-biotin labeled probe, which was chemically synthesized and simply purified, was purchased from Thermo Fisher Scientific. The pool of DNA fragment obtained after the 8th round was amplified via PCR using dDsTP and Diol1-dPxTP to prepare a single-stranded DNA library, the resulting library was diluted with a solution to 100 nM/1× binding solution (20 mM Tris-HCl, 0.5 M NaCl, 10 mM $MgCl_2$. pH 7.6), and 20 µl of the solution was mixed with a biotinylated probe (5 µM, 1 µl). Thereafter, annealing was carried out (90° C. for 3 minutes, gradual cooling at −0.1° C./sec. −55° C. for 15 minutes), and streptavidin magnetic beads in 5 µl of the 1× binding solution was mixed therewith, followed by incubation at 55° C. for 5 minutes. Thus, the biotinylated probe and the DNA fragments complementarily hybridized to the probe were immobilized on the magnetic beads. The solution was removed with the use of a magnetic stand, excess DNA fragments that did not hybridize with the probe were removed, and the magnetic beads were then washed 5 times with 150 µl of the 1× binding solution (55° C.). Thereafter, 20 µl of sterile water was added to the washed magnetic beads, the resultant was heated at 75° C. for 5 minutes, and the solution was recovered immediately thereafter. Thus, the DNA fragments hybridized with the probe were recovered.

When sequencing DNA comprising artificial base(s) sequence patterns vary by adding (Ds), ddPaTP or dPaTP as a substrate complementary to an artificial base (Ds), or ddDsTP or dDsTP as a substrate complementary to Px, which is a base complementary to an artificial base (Ds), during the sequencing reaction using a common dye-terminator. Thus, the presence or absence of an artificial base(s) (Ds) in the DNA fragment used as a sequencing template and an accurate position thereof can be determined. With the use of the DNA fragment recovered using a probe as a template, accordingly. DNA sequencing was performed in accordance with the 2 types of methods (i) and (ii) described below.

(i) With the use of 10 µl of the recovered DNA solution, 15 cycles of PCR was carried out for amplification using AccuPrime Pfx DNA polymerase in the presence of dDsTP and Diol1-dPxTP, then, the DNA fragment recovered via gel purification was dissolved in 20 µl of water. Subsequently the solution was used as a template in the presence of 0.05 mM ddPaTP, 0.05 mM dPaTP, 0.05 mM ddDsTP, or 0.05 mM dDsTP for sequencing. (If the recovered DNA retains an artificial base(s) (Ds). Ds would be retained during PCR according to this method.)

(ii) With the use of 10 µl of the recovered DNA solution, 15 cycle of PCR was carried out for amplification using AccuPrime Pfx DNA polymerase in the presence of 0.05 mM dPaTP, then, the fragment recovered via gel purification was dissolved in 20 µl of water. Subsequently the solution was used as a template in the presence of 0.05 mM ddPaTP, 0.05 mM dPaTP, 0.05 mM ddDsTP, or 0.05 mM dDsTP for sequencing. (If the recovered DNA retains an artificial base(s) (Ds), Ds would be substituted with A or T after PCR according to this method.)

Specifically, DNA sequencing was carried out in 20 µl (in total) using a commercially available BigDye Terminator v1.1 Cycle Sequencing Kit (Thermo Fisher Scientific). With the use of the sequence primers: 5'-ACGACCGT-TCTCTAATTTTGACGTT-3' (SEQ ID NO: 23) and 5'-AC-CAAATTATTGCGATACAGACCCT-3' (SEQ ID NO: 24), the double-stranded DNA fragment amplified by PCR and purified (approximately 0.15 pmol) and ddPaTP or dPaTP, or ddDsTP or dDsTP (500 pmol) were added to the reaction solution, and 25 cycles of PCR (96° C. for 10 seconds, 50° C. for 5 seconds, and 60° C. for 4 minutes) were conducted. The unreacted dye-terminator was removed via desalting column treatment, and the remaining solution was dehydrated under a reduced pressure. A solution of Blue-Dextran diluted in formamide (4 µl) was added to the remnant, and a part thereof was analyzed using the ABI377DNA sequencer. The sequence peak patterns were analyzed using Applied Biosystems PRISM sequencing analysis software v3.2.

As a result of sequence pattern analysis, a pattern (a gap) indicating an artificial base was observed at 3 positions in the sequencing reaction using a Px strand as a template when using artificial base template, whereas peak A was observed in the sequencing reaction when using naturally substituted DNA as a template. This indicates the presence of an artificial base (Ds) at position 19, in addition to the 2 positions of the Ds bases indicated by tag sequences (i.e., 6 and 15 positions in random region).

Example 3: Analysis of Binding Activity of DNA Aptamer Via Gel Shift Assay

In order to examine the binding ability of the sequenced DNA aptamer comprising artificial bases (Ds) at 3 positions to the vWF protein A1 domain, 40-mer and 38-mer DNA aptamers from which the primer regions were cleaved were prepared. Table 2 shows the names and the sequences of the prepared DNA aptamers and FIG. 1 shows the secondary structures deduced based on the nucleotide sequences obtained via selection and the like.

TABLE 2

Sequences of various DNA aptamers used

| SEQ ID NO: | Aptamer name | Sequence (5'→3') |
| --- | --- | --- |
| 1 | vWF1-DsDsDs | TGAGACTCCCCADsCTTTCGCCDsACADsCCGAGGGAGTCTCA |
| 2 | vWF1-DsDsA | TGAGACTCCCCADsCTTTCGCCDsACAACCGAGGGAGTCTCA |
| 3 | vWF1-DsADs | TGAGACTCCCCADsCTTTCGCCAACADsCCGAGGGAGTCTCA |

TABLE 2-continued

Sequences of various DNA aptamers used

| SEQ ID NO: | Aptamer name | Sequence (5'→3') |
|---|---|---|
| 4 | vWF1-ADsDs | TGAGACTCCCCAACTTTCGCCDsACADsCCGAGGGAGTCTCA |
| 5 | vWF1-DsAA | TGAGACTCCCCADsCTTTCGCCAACAACCGAGGGAGTCTCA |
| 6 | vWF1-ADsA | TGAGACTCCCCAACTTTCGCCDsACAACCGAGGGAGTCTCA |
| 7 | vWF1-AADs | TGAGACTCCCCAACTTTCGCCAACADsCCGAGGGAGTCTCA |
| 8 | vWF1-AAA | TGAGACTCCCCAACTTTCGCCAACAACCGAGGGAGTCTCA |
| 9 | vWF1-R1Ds | GAGACTCCCCADsCTTTCGCCDsACAACCGAGGGAGTCTC |
| 10 | ARC1172 | GGCGTGCAGTGCCTTCGGCCGTGCGGTGCCTCCGTCACGCC |
| 11 | vWF1-DsDsDs-GC | CGAGGCTCCCCADsCTTTCGCCDsACADsCCGAGGGAGCCTCG |
| 12 | vWF1-DsDsDs-mhGC | CGAGGCTCCCCADsCTTTCGCCDsACADsCCGAGGGAGCCTCGCGCGTAGCG |

On the basis of vWF1-DsDsDs (SEQ ID NO: 1), 3'-terminal Ds was substituted with A to prepare vWF1-DsDsA (SEQ ID NO: 2), internal Ds was substituted with A to prepare vWF1-DsADs (SEQ ID NO: 3), 5'-terminal Ds was substituted with A to prepare vWF1-ADsDs (SEQ ID NO: 4), internal Ds and 3'-terminal Ds were each substituted with A to prepare vWF1-DsAA (SEQ ID NO: 5), 5'-terminal Ds and 3'-terminal Ds were each substituted with A to prepare vWF1-ADsA (SEQ ID NO: 6), 5'-terminal Ds and internal Ds were each substituted with A to prepare vWF1-AADs (SEQ ID NO: 7), all Ds bases were each substituted with A to prepare vWF1-AAA (SEQ ID NO: 8), and 3'-terminal Ds was substituted with A and the AT pair was removed from the terminal stem region to prepare vWF1-R1Ds (SEQ ID NO: 9). As a positive control, an existing vWF-binding DNA aptamer (i.e., ARC1172; SEQ ID NO: 10) was prepared and used for analysis. The DNA aptamers were chemically synthesized in accordance with a conventional technique.

The binding ability of the synthesized DNA aptamers was analyzed via gel shift assay. Specifically, the DNA aptamers (100 nM) and the vWF A1 domain (100 nM, V003, U-Protein) were suspended in 20 µl of a reaction solution (1×PBS, 0.005% Nonidet P-40), and incubated at 37° C. for 30 minutes. Thereafter, 25% glycerol containing bromophenol blue was added to be a final concentration of glycerol to 5% therein, the resultant was subjected to 8% nondenaturing polyacrylamide gel electrophoresis at 4° C., and the DNA aptamers bound to the vWF A1 domain were separated from the free DNA aptamers. Thereafter, the DNA aptamers were stained with SYBR Gold (Thermo Fisher Scientific) diluted 1/20,000-fold with the 1×TBE solution and detected by a bioimage analyzer (LAS-4000, Fujifilm Corporation). The percentage of gel shifting was determined by dividing the amount of the complex by the amount of the free form and the complex, each deduced based on a band and expressing the determined value in a percentage figure.

Figure 2:
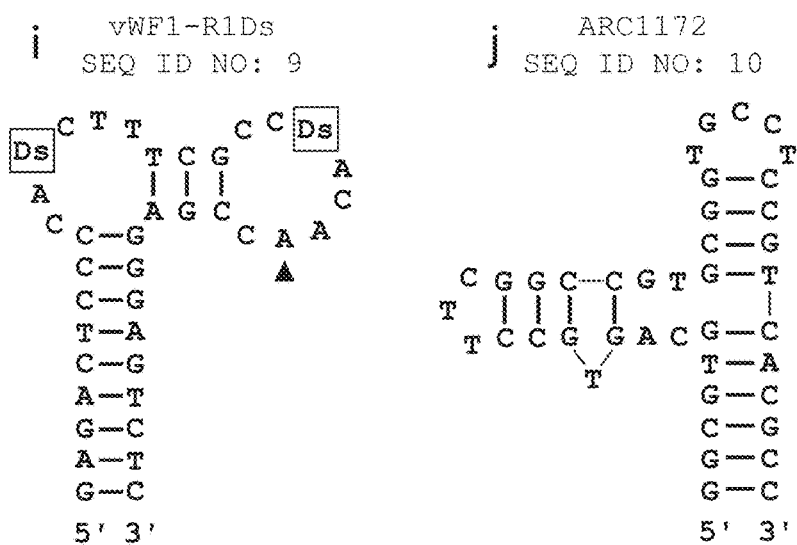

The results are shown in FIG. 2. As a result of gel shift assays, All DNA aptamers in which Ds was substituted with A (i.e., vWF1-DsDsA (b), vWF1-DsADs (c), and vWF1-ADsDs (d)) were observed to have a lower binding activity. This indicates that all the three artificial bases (Ds) are involved in binding. Regarding vWF1-ADsDs (d), the binding ability was not significantly lowered. This indicates that 5'-terminal and internal Ds, in particular, are strongly contributed to binding. In addition, the binding ability of vWF1-DsDsDs (a) was found to be higher than that of the existing vWF-binding DNA aptamer, ARC1172 (j) used as a positive control.

Example 4: Biacore Analysis of Binding Ability of DNA Aptamer to vWF

Figure 3:
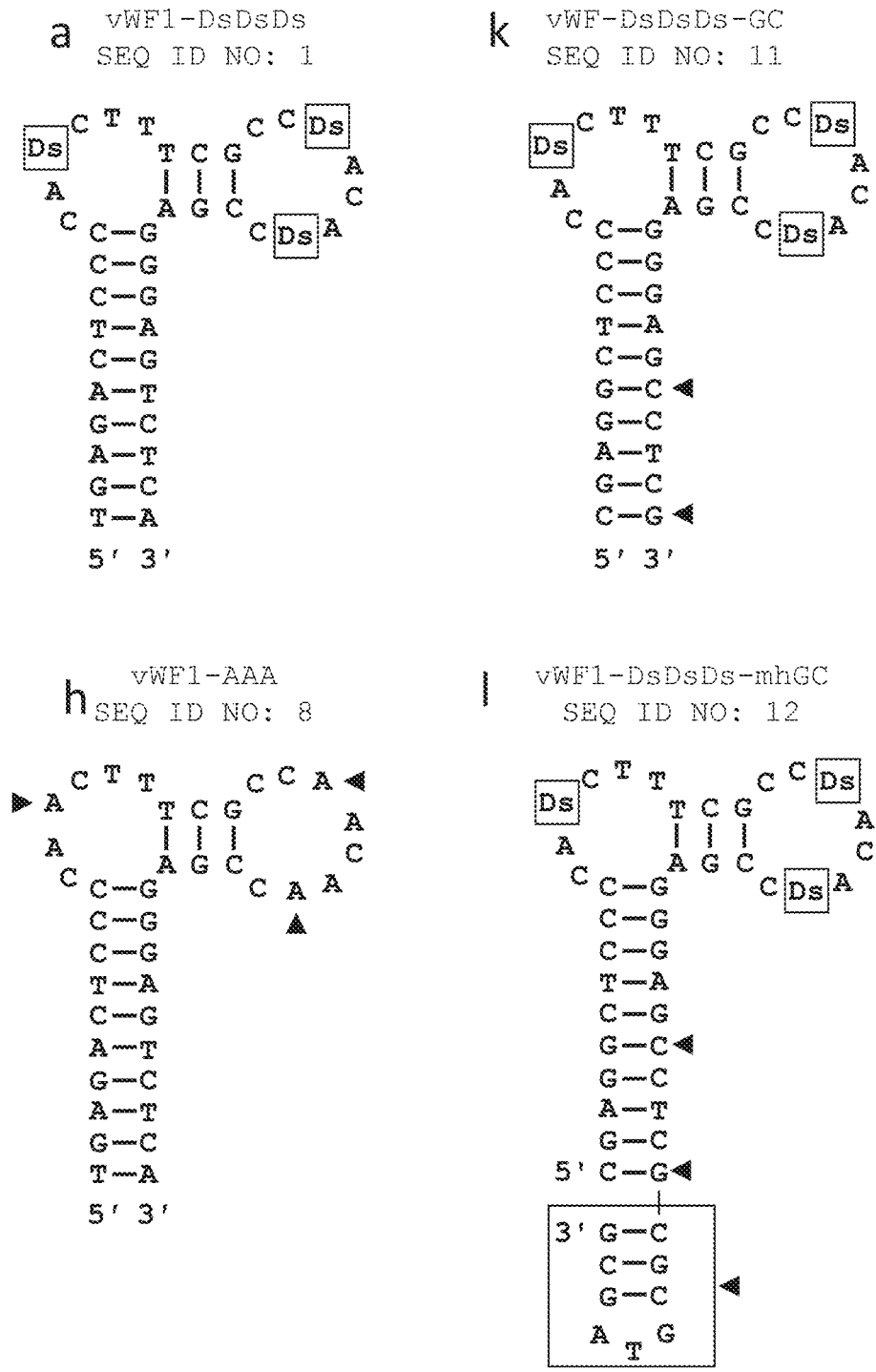
FIG. 3 shows the secondary structures of the DNA aptamers used for binding activity assay via SPR in Example 4. On the basis of vWF1-DsDsDs (SEQ ID NO: 1) shown as "a," 3 Ds bases were each substituted with A to prepare vWF1-AAA (SEQ ID NO: 8) shown as "h," a part of the AT pairs in the stem region was substituted with GC pairs to prepare vWF1-DsDsDs-GC (SEQ ID NO: 11) shown as "k," and a mini-hairpin structure was added to the 3' terminus of vWF1-DsDsDs-GC to prepare vWF1-DsDsDs-mhGC (SEQ ID NO: 12) shown as "l." Ds is boxed, a site at which Ds is substituted with A and a site at which the AT pairs are substituted with the GC pairs are each shown by an arrow head, and a site to which a mini-hairpin structure is added is boxed with an arrow head.

The binding ability of the DNA aptamers was assayed via surface plasmon resonance (SPR) using BiacoreT200 (GE Healthcare). Table 2 shows the sequences of the DNA aptamers used for analysis and FIG. 3 shows the putative secondary structures. On the basis of vWF1-DsDsDs (SEQ ID NO: 1), all of 3 Ds bases were each substituted with A to prepare vWF1-AAA (SEQ ID NO: 8), a part of the AT pairs in the stem region was substituted with the GC pairs to prepare vWF1-DsDsDs-GC (SEQ ID NO: 11), and a mini-hairpin structure was added to the 3' terminus of vWF1-DsDsDs-GC to prepare vWF1-DsDsDs-mhGC (SEQ ID NO: 12). As a positive control, ARC1172 (SEQ ID NO: 10) was used.

These DNA aptamers were prepared by chemical synthesis as biotin-labeled nucleic acids comprising the nucleotide sequences shown in the figure and purified with denaturing acrylamide gel. The nucleic acid fragments were mixed in phosphate buffer (pH 7.4), and the resultant was heated at 95° C., followed by folding (reconstruction) via gradual cooling to 25° C. A streptavidin-coated SA chip (GE Healthcare) was used as an SPR sensor chip, the DNA aptamers were irreversibly immobilized on the chip, and binding thereof to the vWF A1 domain was then analyzed. SPR assay was carried out in a running buffer (a phosphate buffer containing 155 mM NaCl, 0.05% Nonidet P-40) at 37° C. The DNA aptamers were immobilized on a sensor chip by subjecting the DNA solution diluted to 25 nM with a PBS solution to folding treatment (heat-denaturation at 95° C. for 3 minutes, followed by gradual cooling to 25° C.) and then adding Nonidet P-40 to a final concentration of 0.050/%, and then immobilizing the DNA solution (40 µl) on the SA chip via injection at a flow rate of 5 µl/min (equivalent to 8 minutes). Thereafter, 5 µl of a 50 mM NaOH solution was injected thereinto at a flow rate of 20 µl/min 5 times to wash the DNA aptamers non-specifically adsorbed to the SA chip. The interaction between the immobilized DNA aptamer and the vWF A1 domain was monitored by injecting the vWF A1 domain solution (diluted with a running buffer) at 0 nM, 0.3125 nM, 0.625 nM, 1.25 nM, 2.5 nM, 5 nM, 10 nM, and 20 nM in the kinetic injection mode. Assay was carried out at a flow rate of 100 μl/min and a protein injection duration was 150 seconds. The chip was regenerated (i.e., dissociating the bound protein and refolding DNA) by injecting 5 μl of a 50 mM NaOH solution (equivalent to 15 seconds) and flushing the chip with the running buffer for 10 minutes. In order to deduct a response value caused by bulk effects or non-specific adsorption to the sensor chip, the response value of a cell to which no DNA is immobilized (i.e., reference cell) was deducted from the sensorgram of each DNA aptamer.

Figure 4:
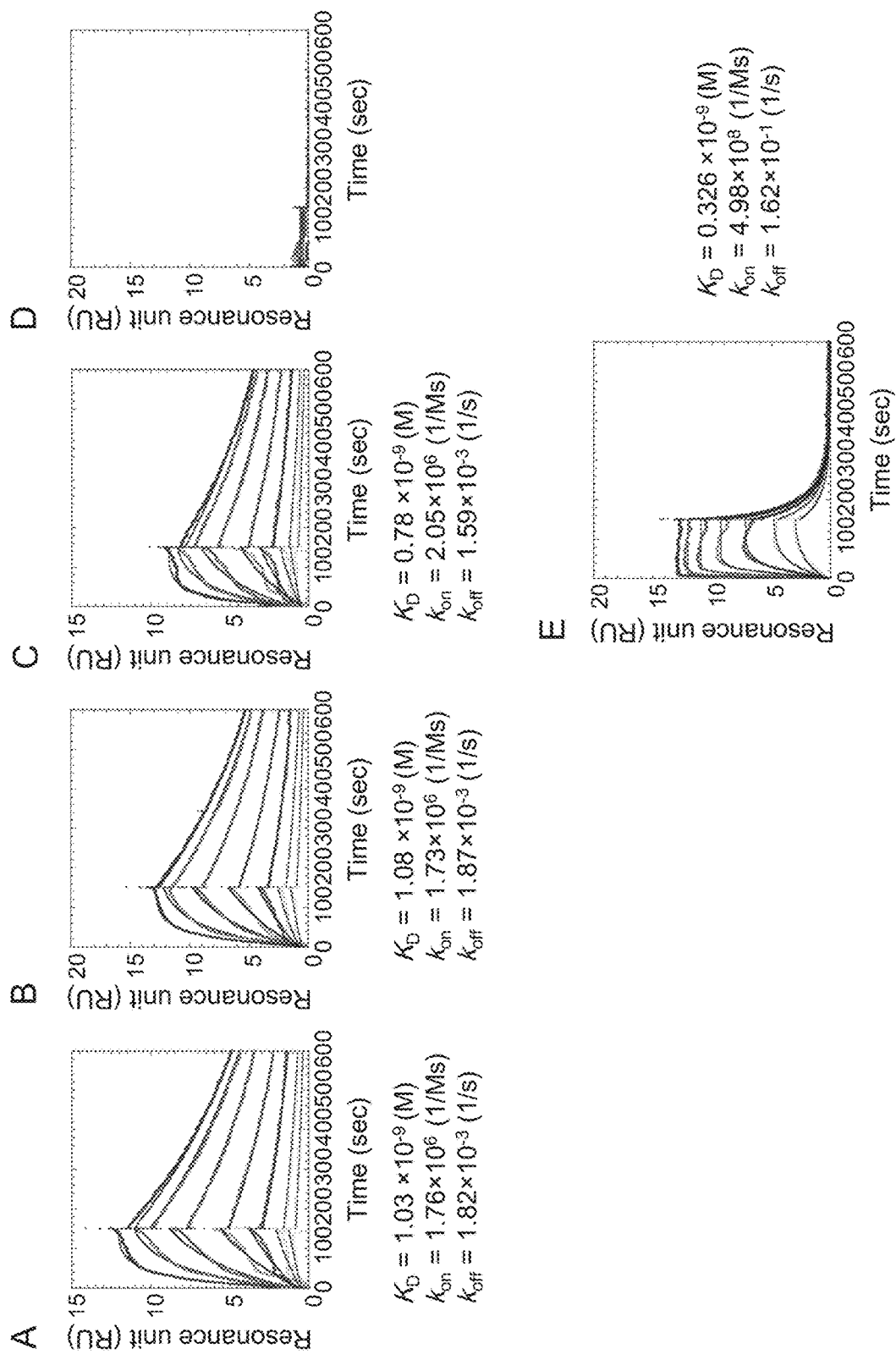
FIG. 4 shows the results of SPR analysis of the DNA aptamers for binding to the A1 domain of the vWF protein. A shows the results of vWF1-DsDsDs, B shows the results of vWF1-DsDsDs-GC, C shows the results of vWF1-DsDsDs-mhGC, D shows the results of vWF1-AAA, and E shows the results of ARC1172.

The results are shown in FIG. 4. As a result of the assay, the $K_D$ values of the DNA aptamers were 1.03 nM (vWF1-DsDsDs), 1.08 nM (vWF1-DsDsDs-GC), and 0.78 nM (vWF1-DsDsDs-GCmh). This indicates that the binding ability was improved by adding mini-hairpin DNA to the 3' terminus. While the $K_D$ value of the DNA aptamer to which mini-hairpin DNA was added (vWF1-DsDsDs-GCmh) was equivalent to the $K_D$ value of conventional ARC1172, the $k_{off}$ value thereof was significantly lower than that of a conventional nucleic acid aptamer (ARC1172: $k_{off}$=0.162 (1/s); vWF1-DsDsDs-GCmh: $k_{off}$=0.00159 (1/s)).

Example 5: Analysis of Tm Value of DNA Aptamer

Figure 5:
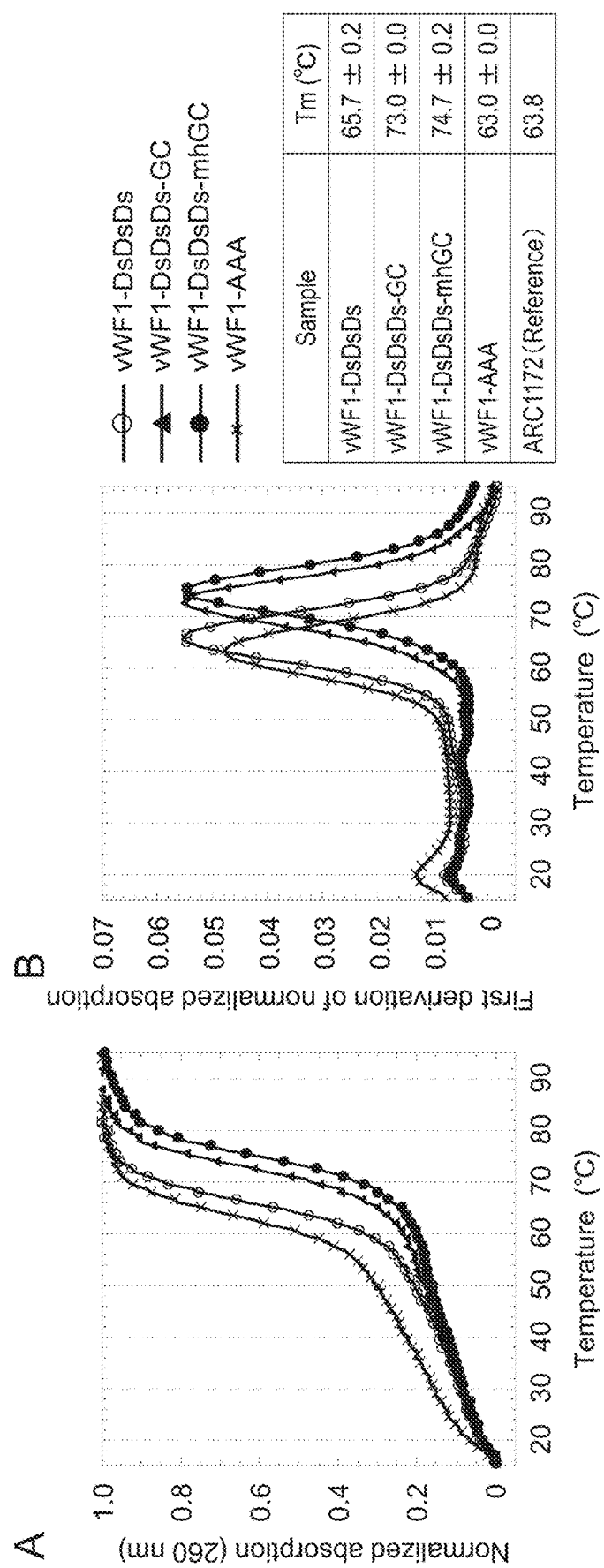
FIG. 5 shows the results of measurement of the Tm values of the DNA aptamers. A shows the normal absorbance of the DNA aptamers at each temperature and B shows the first derivatives of the normalized absorbance of the DNA aptamers at each temperature.

Thermal stability of the DNA aptamers (vWF1-DsDsDs, vWF1-DsDsDs-GC, vWF1-DsDsDs-GCmh. and vWF1-AAA; final concentration: 2 μM) was assayed (Tm values). Changes in the absorbance of the DNA aptamers were assayed using an ultraviolet-visible spectrophotometer UV-2450 (Shimadzu Corporation), and the melting temperature (Tm) was determined from the first derivative thereof. The results are shown in FIG. 5. It was found that Tm of vWF1-DsDsDs was 65.7° C., that of vWF1-DsDsDs-GC was 73.0° C., and that of vWF1-DsDsDs-mhGC was 74.7° C., indicating that thermal stability was improved by increasing GC pairs in the stem region and adding mini-hairpin DNA. In particular, the Tm value of vWF1-DsDsDs-GC and that of vWF1-DsDsDs-mhGC were higher than that of the conventional DNA aptamer (i.e., ARC1172) by 10° C. or more, and thermal stability of vWF1-DsDsDs-GC and vWF1-DsDsDs-mhGC was significantly superior to that of ARC1172. In contrast, vWF1-AAA in which Ds was substituted with A exhibited Tm of 63° C., which was slightly lower than the original level. This indicates that Ds is involved in thermal stability.

Example 6: Selection of DNA Aptamer that Binds to vWF Using Random DNA Library

In accordance with the random library method described in WO 2013/073602, a DNA library containing artificial nucleotide(s) (Ds) was prepared. The library used in the random library method was designed to contain artificial nucleotide (Ds) at random positions in a random nucleotide sequence at a particular proportion. Selection was carried out in accordance with the method of Example 1. Briefly, a DNA fragment (the total number of molecular species: 300 pmol; i.e., about $2\times10^{14}$ molecules) was used as the first-round library, the target protein (i.e., the vWF A1 domain; V003, U-Protein) was mixed therewith. DNA that binds to the target protein was selected and isolated using magnetic beads, the DNA-vWF A1 domain complex was cleaved via polyacrylamide gel electrophoresis to select and isolate the DNA of interest, and the resultant was amplified via PCR. In total, 7 rounds of selection procedures were performed. Table 3 shows the conditions of each selection round. After the completion of 7 rounds of selection, sequence analysis was performed, and the sequences of the DNA aptamers comprising artificial nucleotide(s) (Ds) were obtained.

TABLE 3

Selection conditions

| Round | Method | DNA (nM) | Protein (nM) | Volume (ml) | Competitive molecule (nM) | Number of washing | Gel conditions | Electrophoresis conditions | PCR cycles |
|---|---|---|---|---|---|---|---|---|---|
| 1 | a | 50 | 25 | 6 | — | 5 | — | — | 28 |
| 2 | a | 25 | 10 | 1 | — | 5 | — | — | 25 |
| 3 | a | 5 | 5 | 1 | — | 5 | — | — | 20 |
| 4 | a | 1 | 1 | 3 | 10 | 5 | — | — | 25 |
| 5 | a | 1 | 1 | 3 | 100 | 5 | — | — | 27 |
| 6 | a | 1 | 1 | 3 | 500 | 5 | — | — | 17 |
| 7 | b | 100 | 100 | 0.05 | — | — | Native | 0.5x TBE, 37° C., 300 V, 40 min | 15 |

Method a: Complex biotinylation
Method b: Gel shift separation

As a result of sequence analysis of the DNA library after the 7th round, 151,495 sequences to be analyzed were obtained in total. In accordance with the method of analysis described above, 100 or more clone sequences were extracted, and the number of clones comprising similar sequences was counted. As a result, the most common sequence was a single sequence, which accounted for 44% or more of the whole, and 84% of the whole when similar sequences were included. In the sequences including the most common sequences, there were 3 positions at which only A or T would appear with a high probability.

Example 7: Determination of DNA Aptamer Sequence

The following procedure was carried out in order to accurately identify the positions of artificial base(s) (Ds) and the accurate sequence was determined.

A probe sequence of a DNA fragment consisting of 25 bases that was designed to be specific to the most common sequence obtained in Example 6 was used (5'-CGTT-GAGACCTGTTAGGTGCTCTTC-3': SEQ ID NO: 25). The probe with the biotin-labeled 5' terminus, which was chemically synthesized and simply purified, was purchased from Thermo Fisher Scientific. The target sequence was isolated from the library with using the probe in the same manner as in Example 2.

Sequencing DNA comprising artificial base(s) (Ds) was carried out in the same manner as in Example 2. As a result of sequence pattern analysis, a pattern (a gap) indicating an artificial base was observed at 3 positions in the sequencing reaction using a Px strand as a template when using, whereas peak A was observed in the sequencing reaction when using naturally substituted DNA as a template. This result indicates the presence of artificial bases (Ds) at 3 positions (i.e., 9, 21, and 32 positions in random region).

Example 8: Analysis of Binding Activity of DNA Aptamer Via Gel Shift Assay

In order to examine the binding ability of the sequenced DNA aptamer comprising artificial bases (Ds) at 3 positions to the A1 domain of the vWF protein, a DNA aptamer from which the primer region was cleaved was prepared, and the binding activity was analyzed via gel shift assay. Table 4 shows the sequences of the DNA aptamers used in this example and FIG. 6 shows the putative secondary structures.

Example 9: Biacore Analysis of Binding Ability of DNA Aptamer to vWF

The binding ability of the DNA aptamers was assayed via surface plasmon resonance (SPR) using BiacoreT200 (GE Healthcare). Table 4 shows the sequences of the DNA aptamers used for analysis and FIG. 6 shows the secondary structures deduced based on the nucleotide sequences obtained via selection, and the like.

These DNA aptamer mutants were prepared by chemical synthesis of nucleic acids comprising the nucleotide sequences shown in the figure and purified with denaturing acrylamide gel. The nucleic acid fragments were mixed in phosphate buffer (pH 7.4), and the resultant was heated at 95° C., followed by folding (reconstruction) via gradual cooling to 25° C. Binding analysis via SPR was carried out in the same manner as in Example 4, except that interaction

TABLE 4

Sequences of various DNA aptamers used

| SEQ ID NO: | Aptamer name | Sequence (5'→3') |
|---|---|---|
| 13 | vWF2-DsDsDs | CGTGACCGADsGAGCACCTAACDsGGTCTCAACGDsTGGAGGTCACG |
| 14 | vWF2-DsADs | CGTGACCGADsGAGCACCTAACAGGTCTCAACGDsTGGAGGTCACG |
| 15 | vWF2-DsAA | CGTGACCGADsGAGCACCTAACAGGTCTCAACGATGGAGGTCACG |
| 16 | vWF2-AADs | CGTGACCGAAGAGCACCTAACAGGTCTCAACGDsTGGAGGTCACG |
| 17 | vWF2-AAA | CGTGACCGAAGAGCACCTAACAGGTCTCAACGATGGAGGTCACG |
| 18 | vWF2-DsDsDs-mhGC | CGCGGCCGADsGAGCACCTAACDsGGTCTCAACGDsTGGAGGCCGCGCGCGTAGCG |
| 21 | vWF2-DsDsDs-2mhGC | CGCGGCCGADsGAGCACCGAAGGTCTCAACGDsTGGAGGCCGCGCGCGTAGCG |

On the basis of vWF2-DsDsDs (SEQ ID NO: 13), internal Ds was substituted with A to prepare vWF2-DsADs (SEQ ID NO: 14), internal Ds and 3'-terminal Ds were each substituted with A to prepare vWF2-DsAA (SEQ ID NO: 15), 5'-terminal Ds and internal Ds were each substituted with A to prepare vWF2-AADs (SEQ ID NO: 16), all Ds bases were each substituted with A to prepare vWF2-AAA (SEQ ID NO: 17), and the AT pairs in the stem region were substituted with the GC pairs and mini-hairpin DNA was added to the 3' terminus to prepare vWF2-DsDsDs-mhGC (SEQ ID NO: 18). On the basis of WF2-DsDsDs-mhGC (SEQ ID NO: 18), the internal loop structure of WF2-DsDsDs-mhGC was substituted with the partial sequence of the loop (5'-GAA-3') to prepare vWF2-DsDsDs-2mhGC (SEQ ID NO: 21). A conventional DNA aptamer (ARC1172: SEQ ID NO: 10) was also prepared. The DNA aptamers were chemically synthesized in accordance with a conventional technique.

Gel shift assay was carried out in the same manner as in Example 3, except that electrophoresis was carried out at 4° C. and 300 V, 25° C. and 40 W, and 37° C. and 40 W.

Figure 7:
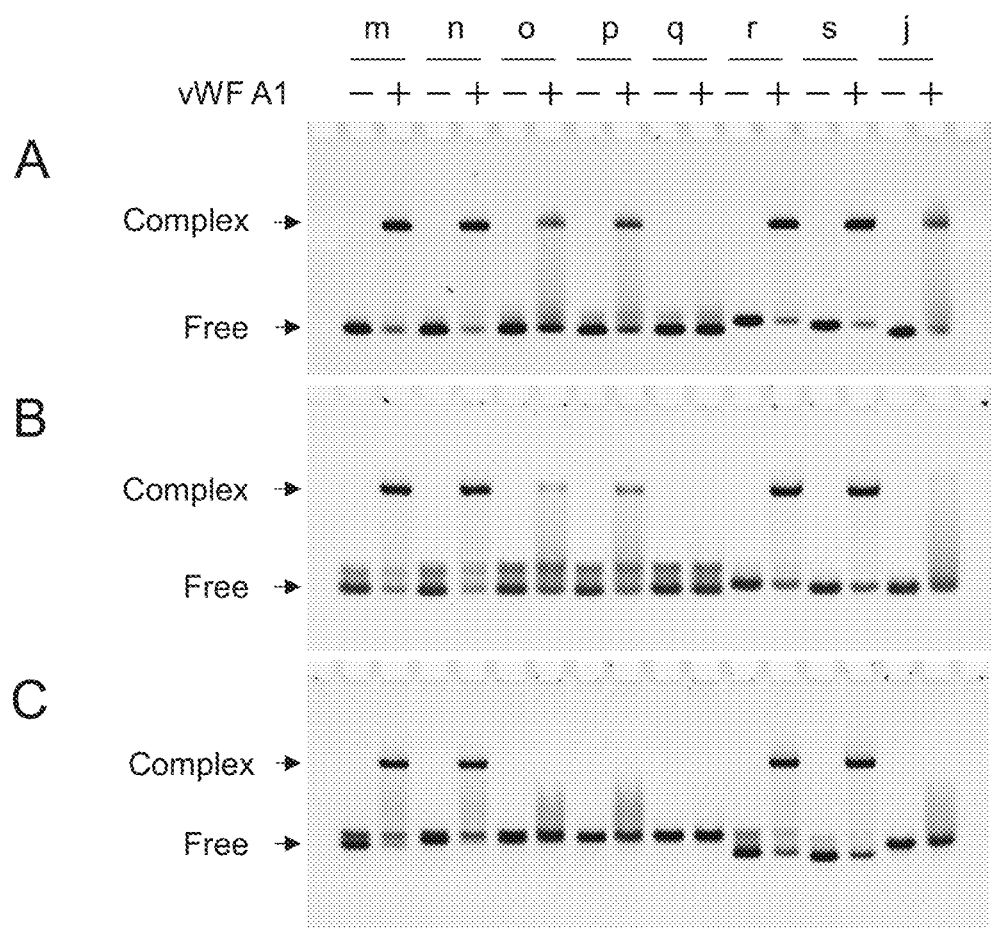
FIG. 7 shows the results of binding analysis (gel shift assays at different temperatures) of the DNA aptamers to the vWF A1 domain via gel shift assays. A to C show the results of DNA aptamer staining with SYBR GOLD upon electrophoresis at 4° C. and 300 V, 25° C. and 40 W, and 37° C. and 40 W, respectively. The complex refers to the DNA aptamer bound to the vWF A1 domain, and the free refers to a free DNA aptamer. "m" to "s" show the results obtained with the use of the aptamers "m" to "s", respectively, shown in FIG. 6-1 and FIG. 6-2. "j" shows the results obtained with the use of ARC1172.

The results are shown in FIG. 7. Gel shift assay indicates that the binding activity of vWF2-DsADs (n) was not decreased in comparison with the activity of vWF2-DsDsDs (m) to vWF A1 domain. And the activity of vWF2-DsAA (o) and vWF2-AADs (p) were decreased in comparison with vWF2-DsDsDs (m). These results indicate that 5'-terminal Ds and 3'-terminal Ds are involved in binding, among 3 artificial bases (Ds). In particular, the binding ability of vWF2-DsAA (o) was significantly lowered, indicating that 3'-terminal Ds is significantly involved in with binding. ARC1172 (j) used as a positive control did not substantially bind to the target when subjected to electrophoresis at 25° C. to 37° C., whereas vWF2-DsDsDs (m), vWF2-DsADs (n), vWF2-DsDsDs-mhGC (r), and vWF2-DsDsDs-2mhGC (s) comprising artificial bases (Ds) maintained the binding activity after electrophoresis at 25° C. to 37° C.

between the DNA aptamer and the vWF A1 domain was detected at 0 nM, 0.078125 nM, 0.15625 nM, 0.3125 nM, 0.625 nM, 1.25 nM, 2.5 nM, and 5 nM.

Figure 8:
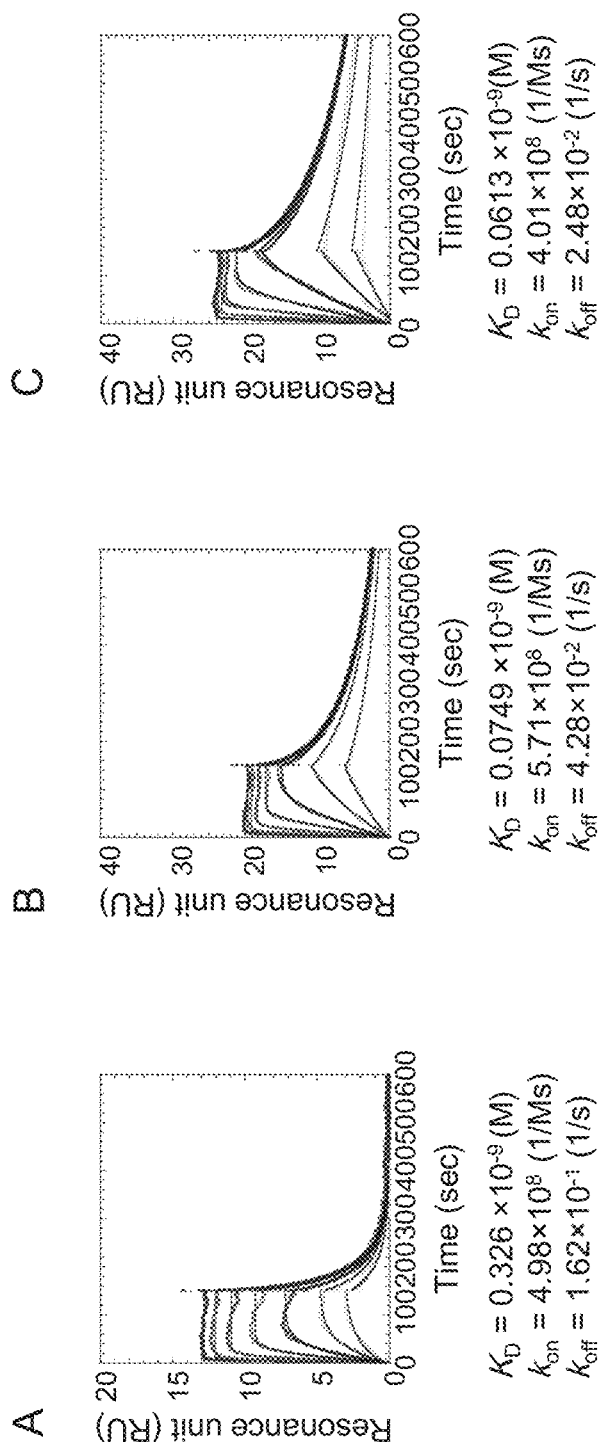
FIG. 8 shows the results of binding analysis via SPR between the DNA aptamers and the A1 domain of the vWF protein. A shows the results of ARC1172, B shows the results of vWF2-DsDsDs, and C shows the results of vWF2-DsDsDs-2mhGC.

The results are shown in FIG. 8. As a result of the measurement, the $K_D$ values of the DNA aptamers were 326 μM (ARC1172), 74.9 μM (vWF2-DsDsDs), and 61.3 μM (Bio-vWF2-DsDsDs-2mhGC). The binding ability was improved by adding mini-hairpin DNA to the 3' terminus, substituting the internal stem-loop structure with the mini-hairpin structure, and substituting the AT pairs with the GC pairs in the stem region. The DNA aptamer comprising artificial base(s) (Ds) obtained in this example was found to have a higher binding ability than the conventional vWF-binding DNA aptamer (ARC1172) used as a positive control (FIG. 8).

Example 10: Analysis of Stability of DNA Aptamer in Human Blood Serum

Stability of the DNA aptamers against nucleases contained in human blood serum was examined. The DNA aptamers (vWF2-DsDsDs, vWF2-DsDsDs-mhGC, vWF2-DsDsDs-2mhGC, vWF2-AAA, and ARC1172; final concentration: 2 μM) were mixed with human blood serum to be the 96% concentration of the human blood serum, and the mixture was incubated at 37° C. 10 μl was taken from the mixture 0, 1, 6, 24, 48, and 72 hours later, and was mixed with 110 μl of a solution of 1×TBE in 10 M urea to terminate the degradation reaction. After the reaction, the sample was separated via denaturing 15% polyacrylamide gel electrophoresis, and the gel was stained with SYBR GOLD (Thermo Fisher Scientific) to detect a single-stranded nucleic acid. The band patterns of the products degraded by nucleases in human blood serum were analyzed using a bioimager LAS-4000 (Fujifilm Corporation).

Figure 9:
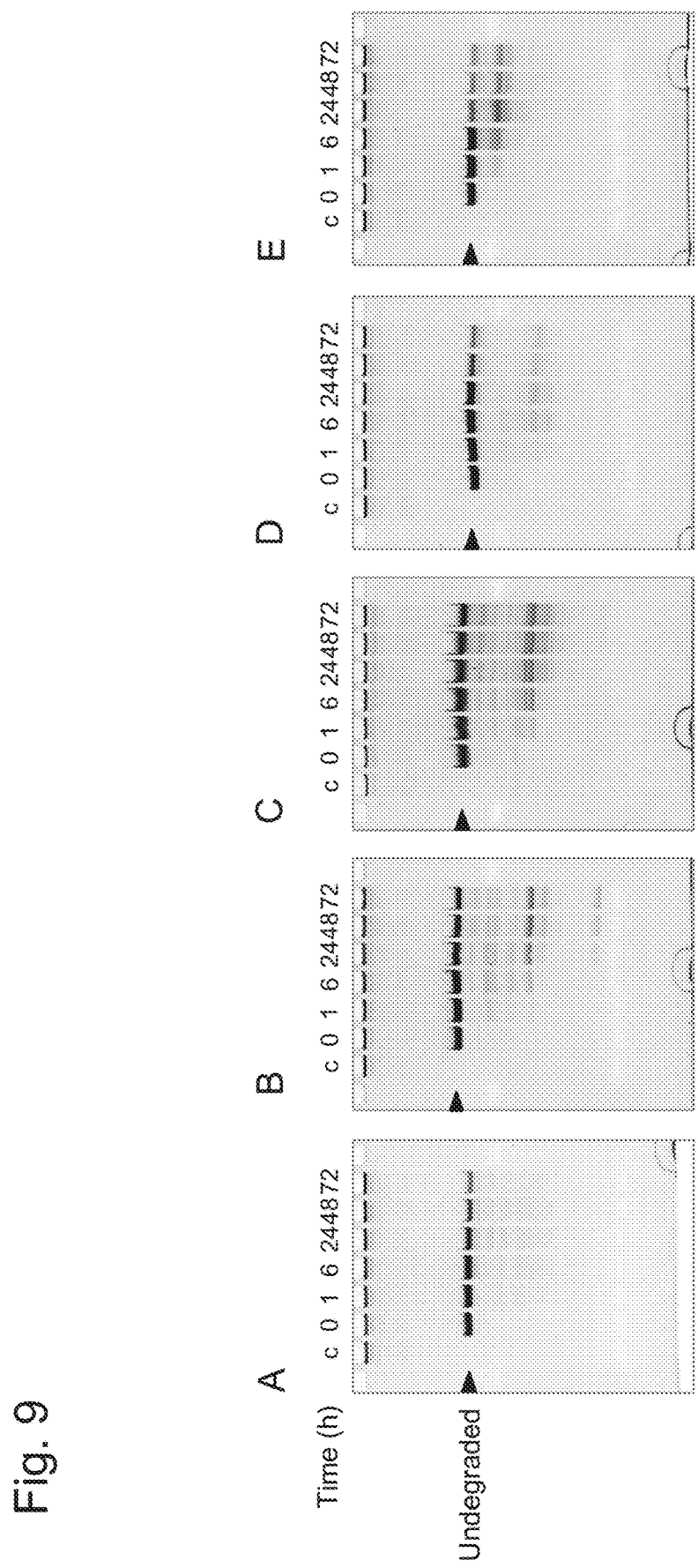
FIG. 9 shows the results of analysis of stability of the DNA aptamers against nucleases in human blood serum. "c" at the left end of the lane indicates a control showing the results of the serum only without the addition of the DNA aptamer. An undegraded band is shown by an arrow head. A shows the results of vWF2-DsDsDs, B shows the results of vWF2-DsDsDs-mhGC, C shows the results of vWF2-DsDsDs-2mhGC, D shows the results of vWF2-AAA, and E shows the results of ARC1172.

The results are shown in FIG. 9. The proportion (%) of the DNA aptamers remaining at each time point deduced based on the intensity of the undegraded band when 0 hour is considered as 100% is shown in Table 5.

TABLE 5

| | Remaining DNA aptamer in blood serum (%) | | | | |
|---|---|---|---|---|---|
| Aptamer name | 1 hour later | 6 hours later | 24 hours later | 48 hours later | 72 hours later |
| vWF2-DsDsDs | 103 | 96 | 69 | 46 | 30 |
| vWF2-DsDsDs-mhGC | 101 | 100 | 78 | 61 | 46 |
| vWF2-DsDsDs-2mhGC | 107 | 111 | 95 | 87 | 75 |
| vWF2-AAA | 103 | 112 | 77 | 42 | 25 |
| ARC1172 | 103 | 91 | 37 | 24 | 20 |

The amount of the remaining full-length DNA aptamers of vWF2-DsDsDs-mhGC and vWF2-DsDsDs-2mhGC is significantly greater than that of vWF-DsDsDs. This indicates that stability of the DNA aptamer against nucleases in blood serum is improved. The amount of remaining ARC1172 used as a positive control was 20% after incubation at 37° C. for 72 hours, whereas 75% of vWF2-DsDsDs-2mhGC remained after 72 hours incubation at 37° C. Thus, the DNA aptamer according to the present invention was shown to have higher stability against nucleases than ARC1172 and its stability against nucleases in blood serum was shown to be significantly improved by adding the mini-hairpin sequence.

Example 11: Analysis of Thermal Stability of DNA Aptamer

Thermal stability (Tm values) of the DNA aptamers (vWF2-DsDsDs, vWF2-DsADs, vWF2-DsAA, vWF2-AADs, vWF2-AAA, vWF2-DsDsDs-mhGC, and vWF2-DsDsDs-2mhGC; final concentration: 2 µM) was assayed. Changes in the absorbance of the DNA aptamers were assayed using an ultraviolet-visible spectrophotometer UV-2450 (Shimadzu Corporation), and the melting temperature (Tm value) was determined from the first derivative thereof.

Figure 10:
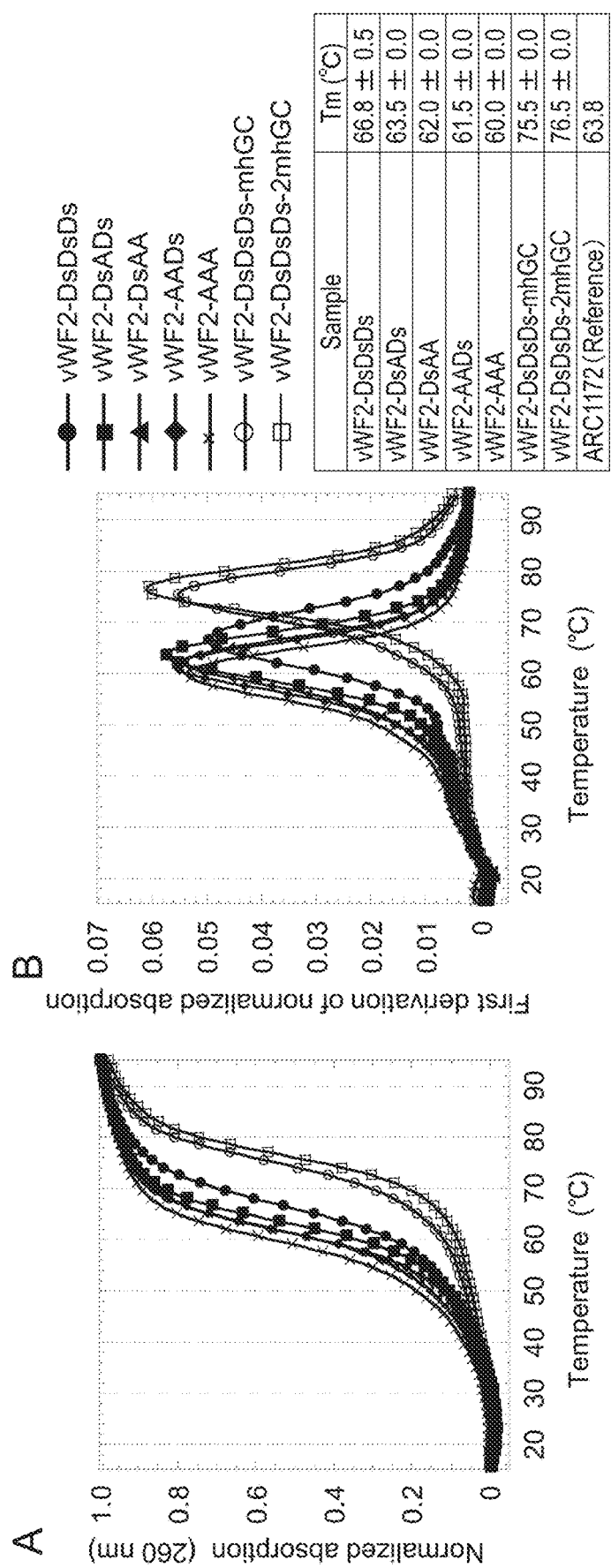
FIG. 10 shows the measurement results of the Tm values of the DNA aptamers. A shows the normal absorbance of the DNA aptamers at each temperature and B shows the first derivatives of the normalized absorbance of the DNA aptamers at each temperature.

The results are shown in FIG. 10. It was found that Tm value of vWF2-DsDsDs was 66.8° C., that of vWF2-DsADs was 63.5° C., that of vWF2-DsAA was 62.0° C., that of vWF2-AADs was 61.5° C., that of vWF2-AAA was 60.0° C., that of vWF2-DsDsDs-mhGC was 75.5° C., and that of vWF2-DsDsDs-2mhGC was 76.5° C. As described above, Tm value was increased by about 9° C. by substituting the AT pairs in the stem sequence with the GC pairs and adding mini-hairpin DNA to the 3' terminus. In addition, Tm value was increased by about 10° C. by substituting the internal stem-loop structure with the mini-hairpin sequence. Thus, a DNA aptamer that remain stable at higher temperatures was prepared.

All publications, patents, and patent applications cited herein are incorporated herein by reference in their entirety.

The invention claimed is:

1. A DNA aptamer that binds to a vWF protein comprising the nucleotide sequence (i) or (ii) below:
   (i) the nucleotide sequence as shown in SEQ ID NO: 18 or 21; or
   (ii) a nucleotide sequence with 75% or more sequence identity to the nucleotide sequence as shown in SEQ ID NO: 18 or 21, wherein an addition, deletion, and/or substitution occurs in the nucleotide sequence as shown in SEQ ID NO: 18 or 21 at position(s) other than that of 7-(2-thienyl)-3H-imidazo[4,5-b]pyridin-3-yl.

* * * * *

SEQUENCE LISTING

```
<160> NUMBER OF SEQ ID NOS: 28

<210> SEQ ID NO 1
<211> LENGTH: 40
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (22)..(22)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (26)..(26)
<223> OTHER INFORMATION: N=7-(2-thienyl)-3H-imidazo[4,5-b]pyridine-3-yl

<400> SEQUENCE: 1
tgagactccc canctttcgc cnacanccga gggagtctca                              40

<210> SEQ ID NO 2
<211> LENGTH: 40
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: N=7-(2-thienyl)-3H-imidazo[4,5-b]pyridine-3-yl
```

<220> FEATURE:
<221> NAME/KEY: misc_feature
<222> LOCATION: (22)..(22)
<223> OTHER INFORMATION: N=7-(2-thienyl)-3H-imidazo[4,5-b]pyridine-3-yl

<400> SEQUENCE: 2
tgagactccc canctttcgc cnacaaccga gggagtctca        40

<210> SEQ ID NO 3
<211> LENGTH: 40
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (26)..(26)
<223> OTHER INFORMATION: N=7-(2-thienyl)-3H-imidazo[4,5-b]pyridine-3-yl

<400> SEQUENCE: 3
tgagactccc canctttcgc caacanccga gggagtctca        40

<210> SEQ ID NO 4
<211> LENGTH: 40
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (22)..(22)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (26)..(26)
<223> OTHER INFORMATION: N=7-(2-thienyl)-3H-imidazo[4,5-b]pyridine-3-yl

<400> SEQUENCE: 4
tgagactccc caactttcgc cnacanccga gggagtctca        40

<210> SEQ ID NO 5
<211> LENGTH: 40
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: N=7-(2-thienyl)-3H-imidazo[4,5-b]pyridine-3-yl

<400> SEQUENCE: 5
tgagactccc canctttcgc caacaaccga gggagtctca        40

<210> SEQ ID NO 6
<211> LENGTH: 40
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (22)..(22)
<223> OTHER INFORMATION: N=7-(2-thienyl)-3H-imidazo[4,5-b]pyridine-3-yl

<400> SEQUENCE: 6
tgagactccc caactttcgc cnacaaccga gggagtctca        40

<210> SEQ ID NO 7
<211> LENGTH: 40
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (26)..(26)
<223> OTHER INFORMATION: N=7-(2-thienyl)-3H-imidazo[4,5-b]pyridine-3-yl

<400> SEQUENCE: 7
tgagactccc caactttcgc caacanccga gggagtctca        40

<210> SEQ ID NO 8
<211> LENGTH: 40
<212> TYPE: DNA
<213> ORGANISM: Artificial
<220> FEATURE:
<223> OTHER INFORMATION: Synthetic Construct

<400> SEQUENCE: 8
tgagactccc caactttcgc caacaaccga gggagtctca        40

<210> SEQ ID NO 9
<211> LENGTH: 38
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (12)..(12)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (21)..(21)
<223> OTHER INFORMATION: N=7-(2-thienyl)-3H-imidazo[4,5-b]pyridine-3-yl

<400> SEQUENCE: 9
gagactcccc anctttcgcc nacaaccgag ggagtctc        38

<210> SEQ ID NO 10
<211> LENGTH: 41
<212> TYPE: DNA
<213> ORGANISM: Artificial
<220> FEATURE:
<223> OTHER INFORMATION: Synthetic Construct

<400> SEQUENCE: 10
ggcgtgcagt gccttcggcc gtgcggtgcc tccgtcacgc c        41

<210> SEQ ID NO 11
<211> LENGTH: 40
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (22)..(22)
<223> OTHER INFORMATION: N=7-(2-thienyl)-3H-imidazo[4,5-b]pyridine-3-yl
<220> FEATURE:
<221> NAME/KEY: misc_feature

```
<222> LOCATION: (26)..(26)
<223> OTHER INFORMATION: N=7-(2-thienyl)-3H-imidazo[4,5-b]pyridine-3-yl

<400> SEQUENCE: 11
cgaggctccc canctttcgc cnacanccga gggagcctcg                                40

<210> SEQ ID NO 12
<211> LENGTH: 49
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (22)..(22)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (26)..(26)
<223> OTHER INFORMATION: N=7-(2-thienyl)-3H-imidazo[4,5-b]pyridine-3-yl

<400> SEQUENCE: 12
cgaggctccc canctttcgc cnacanccga gggagcctcg cgcgtagcg                      49

<210> SEQ ID NO 13
<211> LENGTH: 44
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (22)..(22)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (33)..(33)
<223> OTHER INFORMATION: N=7-(2-thienyl)-3H-imidazo[4,5-b]pyridine-3-yl

<400> SEQUENCE: 13
cgtgaccgan gagcacctaa cnggtctcaa cgntggaggt cacg                           44

<210> SEQ ID NO 14
<211> LENGTH: 44
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (33)..(33)
<223> OTHER INFORMATION: N=7-(2-thienyl)-3H-imidazo[4,5-b]pyridine-3-yl

<400> SEQUENCE: 14
cgtgaccgan gagcacctaa caggtctcaa cgntggaggt cacg                           44

<210> SEQ ID NO 15
<211> LENGTH: 44
<212> TYPE: DNA
```

<210> SEQ ID NO 15 (continued)
<213> ORGANISM: Artificial
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: N=7-(2-thienyl)-3H-imidazo[4,5-b]pyridine-3-yl

<400> SEQUENCE: 15
cgtgaccgan gagcacctaa caggtctcaa cgatggaggt cacg            44

<210> SEQ ID NO 16
<211> LENGTH: 44
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (33)..(33)
<223> OTHER INFORMATION: N=7-(2-thienyl)-3H-imidazo[4,5-b]pyridine-3-yl

<400> SEQUENCE: 16
cgtgaccgaa gagcacctaa caggtctcaa cgntggaggt cacg            44

<210> SEQ ID NO 17
<211> LENGTH: 44
<212> TYPE: DNA
<213> ORGANISM: Artificial
<220> FEATURE:
<223> OTHER INFORMATION: Synthetic Construct

<400> SEQUENCE: 17
cgtgaccgaa gagcacctaa caggtctcaa cgatggaggt cacg            44

<210> SEQ ID NO 18
<211> LENGTH: 53
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (22)..(22)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (33)..(33)
<223> OTHER INFORMATION: N=7-(2-thienyl)-3H-imidazo[4,5-b]pyridine-3-yl

<400> SEQUENCE: 18
cgcggccgan gagcacctaa cnggtctcaa cgntggaggc cgcgcgcgta gcg       53

<210> SEQ ID NO 19
<211> LENGTH: 44
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (22)..(22)
<223> OTHER INFORMATION: N=7-(2-thienyl)-3H-imidazo[4,5-b]pyridine-3-yl

```
<220> FEATURE:
<221> NAME/KEY: misc_feature
<222> LOCATION: (33)..(33)
<223> OTHER INFORMATION: N=7-(2-thienyl)-3H-imidazo[4,5-b]pyridine-3-yl

<400> SEQUENCE: 19
cgcggccgan gagcacctaa cnggtctcaa cgntggaggc cgcg                44

<210> SEQ ID NO 20
<211> LENGTH: 42
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (31)..(31)
<223> OTHER INFORMATION: N=7-(2-thienyl)-3H-imidazo[4,5-b]pyridine-3-yl

<400> SEQUENCE: 20
cgcggccgan gagcaccgaa ggtctcaacg ntggaggccg cg                  42

<210> SEQ ID NO 21
<211> LENGTH: 51
<212> TYPE: DNA
<213> ORGANISM: Artificial
<220> FEATURE:
<223> OTHER INFORMATION: Synthetic Construct
<220> FEATURE:
<221> NAME/KEY: misc_feature
<222> LOCATION: (10)..(10)
<223> OTHER INFORMATION: N=7-(2-thienyl)-3H-imidazo[4,5-b]pyridine-3-yl
<220> FEATURE:
<221> NAME/KEY: misc_feature
<222> LOCATION: (31)..(31)
<223> OTHER INFORMATION: N=7-(2-thienyl)-3H-imidazo[4,5-b]pyridine-3-yl

<400> SEQUENCE: 21
cgcggccgan gagcaccgaa ggtctcaacg ntggaggccg cgcgcgtagc g         51

<210> SEQ ID NO 22
<211> LENGTH: 26
<212> TYPE: DNA
<213> ORGANISM: Artificial
<220> FEATURE:
<223> OTHER INFORMATION: Synthetic Construct

<400> SEQUENCE: 22
actccctcgg ttgttggcga aagttg                                    26

<210> SEQ ID NO 23
<211> LENGTH: 25
<212> TYPE: DNA
<213> ORGANISM: Artificial
<220> FEATURE:
<223> OTHER INFORMATION: Primer

<400> SEQUENCE: 23
acgaccgttc tctaattttg acgtt                                     25

<210> SEQ ID NO 24
<211> LENGTH: 25
<212> TYPE: DNA
<213> ORGANISM: Artificial
<220> FEATURE:
```

<223> OTHER INFORMATION: Primer

<400> SEQUENCE: 24
accaaattat tgcgatacag accct                                          25

<210> SEQ ID NO 25
<211> LENGTH: 25
<212> TYPE: DNA
<213> ORGANISM: Artificial
<220> FEATURE:
<223> OTHER INFORMATION: Synthetic Construct

<400> SEQUENCE: 25
cgttgagacc tgttaggtgc tcttc                                          25

<210> SEQ ID NO 26
<211> LENGTH: 9
<212> TYPE: DNA
<213> ORGANISM: Artificial
<220> FEATURE:
<223> OTHER INFORMATION: Synthetic Construct

<400> SEQUENCE: 26 cgcgtagcg                                                             9

<210> SEQ ID NO 27
<211> LENGTH: 8442
<212> TYPE: DNA
<213> ORGANISM: Homo sapiens

<400> SEQUENCE: 27
atgattcctg ccagatttgc cggggtgctg cttgctctgg ccctcatttt gccagggacc    60
ctttgtgcag aaggaactcg cggcaggtca tccacggccc gatgcagcct tttcggaagt   120
gacttcgtca cacctttga tgggagcatg tacagctttg cgggatactg cagttacctc   180
ctggcagggg gctgccagaa cgctccttc tcgattattg gggacttcca gaatggcaag   240
agagtgagcc tctccgtgta tcttggggaa ttttttgaca tccatttgtt tgtcaatggt   300
accgtgacac aggggaccca agagtctccc atgccctatg cctccaaagg ctgtatcta   360 gaaactgagg ctgggtacta caagctgtcc ggtgaggcct atggctttgt ggccaggatc   420
gatggcagcg gcaactttca gtcctgctg tcagacagat acttcaacaa gacctgcggg   480
ctgtgtggca actttaacat cttttgctga agatgacttta tgacccaaga agggaccttg   540
acctcggacc cttatgactt tgccaactca tgggctctga gcagtggaga cagtggtgt   600 gaacgggcat ctcctcccag cagctcatgc aacatctcct ctgggaaat gcagaagggc   660 ctgtgggagc agtgccagct tctgaagagc acctcggtgt ttgcccgctg ccaccctctg   720
gtggaccccg agccttttgt ggccctgtgt gagaagactt tgtgtgagtg tgctgggggg   780
ctggagtgcg cctgccctgc cctcctggag tacgcccgga cctgtgccca ggagggaatg   840
gtgctgtacg gctggaccga ccacagcgcg tgcagcccag tgtgccctgc tggtatggag   900
tataggcagt gtgtgtcccc ttgcgccagg acctgccaga gcctgcacat caatgaaatg   960
tgtcaggagc gatgcgtgga tgctgcagc tgccctgagg acagctcct ggatgaaggc   1020 ctctgcgtgg agagcaccga gtgtccctgc gtgcattccg aaagcgcta ccctcccggc   1080 acctccctct ctcgagactg caacacctgc atttgccgaa acagccagtg gatctgcagc   1140
aatgaagaat gtccagggga gtgccttgtc acaggtcaat cacacttcaa gagctttgac   1200
aacagatact tcaccttcag tgggatctgc cagtacctgc tggcccggga ttgccagga c   1260

```
cactccttct ccattgtcat tgagactgtc cagtgtgctg atgaccgcga cgctgtgtgc   1320
acccgctccg tcaccgtccg gctgcctggc ctgcacaaca gccttgtgaa actgaagcat   1380
ggggcaggag ttgccatgga tggccaggac gtccagctcc ccctcctgaa aggtgacctc   1440
cgcatccagc atacagtgac ggcctccgtg cgcctcagct acggggagga cctgcagatg   1500
gactgggatg gccgcgggag gctgctggtg aagctgtccc ccgtctatgc cgggaagacc   1560
tgcggcctgt gtgggaatta caatggcaac cagggcgacg acttccttac ccctctgg   1620 ctggcggagc cccgggtgga ggacttcggg aacgcctgga agctgcacgg ggactgccag   1680
gacctgcaga agcagcacag cgatccctgc ccctcaacc cgcgcatgac caggttctcc   1740
gaggaggcgt gcgcggtcct gacgtccccc acattcgagg cctgccatcg tgccgtcagc   1800
ccgctgccct acctgcggaa ctgccgctac gacgtgtgct cctgctcgga cggccgcgag   1860
tgcctgtgcg cgccctggc cagctatgcc gcggcctgcg cggggagagg cgtgcgcgtc   1920
gcgtggcgcg agccaggccg ctgtgagctg aactgcccga aggccaggt gtacctgcag   1980 tgcgggaccc cctgcaacct gacctgccgc tctctctctt acccggatga ggaatgcaat   2040
gaggcctgcc tggagggctg cttctgcccc ccagggctct acatggatga gggggggac   2100 tgcgtgccca aggcccagtg cccctgttac tatgacggtg agatcttcca gccagaagac   2160
atcttctcag accatcacac catgtgctac tgtgaggatg gcttcatgca ctgtaccatg   2220
agtggagtcc ccggaagctt gctgcctgac gctgtcctca gcagtcccct gtctcatcgc   2280
agcaaaagga gcctatcctg tcggcccccc atggtcaagc tggtgtgtcc cgctgacaac   2340
ctgcgggctg aagggctcga gtgtaccaaa acgtgccaga actatgacct ggagtgcatg   2400
agcatgggct gtgtctctgg ctgcctctgc ccccgggca tggtccggca tgagaacaga   2460
tgtgtggccc tggaaaggtg tccctgcttc catcagggca aggagtatgc ccctggagaa   2520
acagtgaaga ttggctgcaa cacttgtgtc tgtcgggacc ggaagtggaa ctgcacagac   2580
catgtgtgtg atgccacgtg ctccacgatc ggcatggccc actacctcac cttcgacggg   2640
ctcaaatacc tgttccccgg ggagtgccag tacgttctgg tgcaggatta ctgcggcagt   2700
aaccctggga cctttcggat cctagtgggg aataagggat gcagccaccc ctcagtgaaa   2760
tgcaagaaac gggtcaccat cctggtggag ggaggagaga ttgagctgtt tgacggggag   2820
gtgaatgtga agaggcccat gaaggatgag actcactttg aggtggtgga gtctggccgg   2880
tacatcattc tgctgctggg caaagccctc tccgtggtct gggaccgcca cctgagcatc   2940
tccgtggtcc tgaagcagac ataccaggag aaagtgtgtg gcctgtgtgg gaattttgat   3000
ggcatccaga caatgaccct caccagcagc aacctccaag tggaggaaga ccctgtggac   3060
tttgggaact cctggaaagt gagctcgcag tgtgctgaca ccagaaaagt gcctctggac   3120
tcatcccctg ccacctgcca taacaacatc atgaagcaga cgatggtgga ttcctcctgt   3180
agaatcctta ccagtgacgt cttccaggac tgcaacaagc tggtgacccc cgagccatat   3240
ctggatgtct gcatttacga cacctgctcc tgtgagtcca ttggggactg cgcctgcttc   3300
tgcgacacca ttgctgccta tgcccacgtg tgtgcccagc atggcaaggt ggtgacctgg   3360
aggacggcca cattgtgccc ccagagctgc gaggagagga atctccggga gaacgggtat   3420
gagtgtgagt ggcgctataa cagctgtgca cctgcctgtc aagtcacgtg tcagcaccct   3480
gagccactgg cctgccctgt gcagtgtgtg gagggctgcc atgccactg ccctccaggg   3540 aaaatcctgg atgagctttt gcagacctgc gttgaccctg aagactgtcc agtgtgtgag   3600
```

```
gtggctggcc ggcgttttgc ctcaggaaag aaagtcacct tgaatcccag tgaccctgag    3660
cactgccaga tttgccactg tgatgttgtc aacctcacct gtgaagcctg ccaggagccg    3720
ggaggcctgg tggtgcctcc cacagatgcc ccggtgagcc ccaccactct gtatgtggag    3780
gacatctcgg aaccgccgtt gcacgatttc tactgcagca ggctactgga cctggtcttc    3840
ctgctggatg gctcctccag gctgtccgag gctgagtttg aagtgctgaa ggcctttgtg    3900
gtggacatga tggagcggct gcgcatctcc cagaagtggg tccgcgtggc cgtggtggag    3960
taccacgacg gctcccacgc ctacatcggg ctcaaggacc ggaagcgacc gtcagagctg    4020
cggcgcattg ccagccaggt gaagtatgcg ggcagccagg tggcctccac cagcgaggtc    4080
ttgaaataca cactgttcca aatcttcagc aagatcgacc gccctgaagc ctcccgcatc    4140
accctgctcc tgatggccag ccaggagccc aacggatgt  cccggaactt tgtccgctac    4200
gtccagggcc tgaagaagaa gaaggtcatt gtgatcccgg tgggcattgg gcccatgcc    4260 aacctcaagc agatccgcct catcgagaag caggcccctg agaacaaggc cttcgtgctg    4320
agcagtgtgg atgagctgga gcagcaaagg gacgagatcc ttagctacct ctgtgacctt    4380 gccctgaag cccctcctcc tactctgccc ccgacatgg cacaagtcac tgtgggcccg    4440
gggctcttgg gggtttcgac cctggggccc aagaggaact ccatggttct ggatgtggcg    4500
ttcgtcctgg aaggatcgga caaaattggt gaagccgact tcaacaggag caaggagttc    4560
atggaggagg tgattcagcg gatggatgtg gccaggaca  gcatccacgt cacggtgctg    4620
cagtactcct acatggtgac tgtggagtac cccttcagcg aggcacagtc caaaggggac    4680
atcctgcagc gggtgcgaga gatccgctac cagggcggca acaggaccaa cactgggctg    4740
gccctgcggt acctctctga ccacagcttc ttggtcagcc agggtgaccg ggagcaggcg    4800
cccaacctgg tctacatggt caccggaaat cctgcctctg atgagatcaa gaggctgcct    4860
ggagacatcc aggtggtgcc cattggagtg ggccctaatg ccaacgtgca ggagctggag    4920
aggattggct ggcccaatgc ccctatcctc atccaggact ttgagacgct ccccgagag    4980 gctcctgacc tggtgctgca gaggtgctgc tccggagagg ggctgcagat ccccaccctc    5040 tccctgcac ctgactgcag ccagcccctg gacgtgatcc ttctcctgga tggctcctcc    5100
agtttcccag cttcttattt tgatgaaatg aagagtttcg ccaaggcttt catttcaaaa    5160
gccaatatag ggcctcgtct cactcaggtg tcagtgctgc agtatggaag catcaccacc    5220
attgacgtgc catggaacgt ggtcccggag aaagcccatt tgctgagcct tgtggacgtc    5280
atgcagcggg agggaggccc cagccaaatc ggggatgcc  tgggctttgc tgtgcgatac    5340
ttgacttcag aaatgcatgg tgccaggccg ggagcctcaa aggcggtggt catcctggtc    5400
acggacgtct ctgtggattc agtggatgca gcagctgatg ccgccaggtc caacagagtg    5460
acagtgttcc ctattggaat tggagatcgc tacgatgcag cccagctacg gatcttggca    5520 ggccagcag  gcgactccaa cgtggtgaag ctccagcgaa tcgaagacct ccctaccatg    5580
gtcaccttgg gcaattcctt cctccacaaa ctgtgctctg gatttgttag gatttgcatg    5640
gatgaggatg ggaatgagaa gaggcccggg gacgtctgga ccttgccaga ccagtgccac    5700
accgtgactt gccagccaga tggccagacc ttgctgaaga gtcatcgggt caactgtgac    5760
cgggggctga ggccttcgtg ccctaacagc cagtcccctg ttaaagtgga agagacctgt    5820
ggctgccgct ggacctgccc ctgcgtgtgc acaggcagct ccactcggca catcgtgacc    5880
tttgatgggc agaatttcaa gctgactggc agctgttctt atgtcctatt tcaaaacaag    5940
gagcaggacc tggaggtgat tctccataat ggtgcctgca gccctggagc aaggcagggc    6000
```

-continued

```
tgcatgaaat ccatcgaggt gaagcacagt gccctctccg tcgagctgca cagtgacatg    6060
gaggtgacgg tgaatgggag actggtctct gttccttacg tgggtgggaa catggaagtc    6120
aacgtttatg gtgccatcat gcatgaggtc agattcaatc accttggtca catcttcaca    6180
ttcactccac aaaacaatga gttccaactg cagctcagcc ccaagacttt tgcttcaaag    6240
acgtatggtc tgtgtgggat ctgtgatgag aacggagcca atgacttcat gctgagggat    6300
ggcacagtca ccacagactg aaaacacttt gttcaggaat ggactgtgca gcggccaggg    6360
cagacgtgcc agcccatcct ggaggagcag tgtcttgtcc ccgacagctc ccactgccag    6420
gtcctcctct taccactgtt tgctgaatgc acaaggtcc tggctccagc acattctat    6480 gccatctgcc agcaggacag ttgccaccag gagcaagtgt gtgaggtgat cgcctcttat    6540
gcccacctct gtcggaccaa cggggtctgc gttgactgga ggacacctga tttctgtgct    6600
atgtcatgcc caccatctct ggtctacaac cactgtgagc atggctgtcc ccggcactgt    6660
gatggcaacg tgagctcctg tggggaccat ccctccgaag ctgtttctg ccctccagat    6720 aaagtcatgt tggaaggcag ctgtgtccct gaagaggcct gcactcagtg cattggtgag    6780
gatggagtcc agcaccagtt cctggaagcc tgggtcccgg accaccagcc tgtcagatc    6840 tgcacatgcc tcagcgggcg gaaggtcaac tgcacaacgc agccctgccc cacggccaaa    6900
gctcccacgt gtgcctgtg tgaagtagcc cgcctccgcc agaatgcaga ccagtgctgc    6960
cccgagtatg agtgtgtgtg tgacccagtg agctgtgacc tgccccagt gcctcactgt    7020 gaacgtggcc tccagcccac actgaccaac cctggcgagt gcagaccaa cttcacctgc    7080 gcctgcagga aggaggagtg caaaagagtg tccccaccct cctgccccc gcaccgtttg    7140 cccacccttc ggaagaccca gtgctgtgat gagtatgagt gtgcctgcaa ctgtgtcaac    7200
tccacagtga gctgtcccct tgggtacttg gcctcaactg ccaccaatga ctgtggctgt    7260
accacaacca cctgccttcc cgacaaggtg tgtgtccacc gaagcaccat ctaccctgtg    7320
ggccagttct gggaggaggg ctgcgatgtg tgcacctgca ccgacatgga ggatgccgtg    7380
atgggcctcc gcgtggccca gtgctccag aagccctgtg aggacagctg tcggtcgggc    7440
ttcacttacg ttctgcatga aggcgagtgc tgtggaaggt gcctgccatc tgcctgtgag    7500
gtggtgactg gctcaccgcg gggggactcc cagtcttcct ggaagagtgt cggctcccag    7560
tgggcctccc cggagaaccc ctgcctcatc aatgagtgtg tccgagtgaa ggaggaggtc    7620
tttatacaac aaaggaacgt ctcctgcccc cagctggagg tccctgtctg cccctcgggc    7680
tttcagctga gctgtaagac ctcagcgtgc tgcccaagct gtcgctgtga gcgcatggag    7740
gcctgcatgc tcaatggcac tgtcattggg cccgggaaga ctgtgatgat cgatgtgtgc    7800
acgacctgcc gctgcatggt gcaggtgggg gtcatctctg gattcaagct ggagtgcagg    7860
aagaccacct gcaacccctg ccccctgggt tacaaggaag aaaataacac aggtgaatgt    7920
tgtgggagat gtttgcctac ggcttgcacc attcagctaa gaggaggaca gatcatgaca    7980
ctgaagcgtg atgagacgct ccaggatggc tgtgatactc acttctgcaa ggtcaatgag    8040
agaggagagt acttctggga gaagagggtc acaggctgcc caccctttga tgaacacaag    8100
tgtctggctg agggaggtaa aattatgaaa attccaggca cctgctgtga cacatgtgag    8160
gagcctgagt gcaacgacat cactgccagg ctgcagtatg tcaaggtggg aagctgtaag    8220
tctgaagtag aggtggatat ccactactgc cagggcaaat gtgccagcaa agccatgtac    8280
tccattgaca tcaacgatgt gcaggaccag tgctcctgct gctctccgac acggacggag    8340
```

```
cccatgcagg tggccctgca ctgcaccaat ggctctgttg tgtaccatga ggttctcaat    8400
gccatggagt gcaaatgctc ccccaggaag tgcagcaagt ga                       8442
```

<210> SEQ ID NO 28
<211> LENGTH: 2813
<212> TYPE: PRT
<213> ORGANISM: Homo sapiens

<400> SEQUENCE: 28

```
Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
            20                  25                  30

Ala Arg Cys Ser Leu Phe Gly Ser Asp Phe Val Asn Thr Phe Asp Gly
        35                  40                  45

Ser Met Tyr Ser Phe Ala Gly Tyr Cys Ser Tyr Leu Leu Ala Gly Gly
    50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125

Leu Ser Gly Glu Ala Tyr Gly Phe Val Ala Arg Ile Asp Gly Ser Gly
    130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
        195                 200                 205

Ser Cys Asn Ile Ser Ser Gly Glu Met Gln Lys Gly Leu Trp Glu Gln
    210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
            260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
            340                 345                 350

Ser Gly Lys Arg Tyr Pro Pro Gly Thr Ser Leu Ser Arg Asp Cys Asn
```

```
                355                 360                 365
Thr Cys Ile Cys Arg Asn Ser Gln Trp Ile Cys Ser Asn Glu Glu Cys
        370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
            420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
            500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
            580                 585                 590

Glu Ala Cys His Arg Ala Val Ser Pro Leu Pro Tyr Leu Arg Asn Cys
        595                 600                 605

Arg Tyr Asp Val Cys Ser Cys Ser Asp Gly Arg Glu Cys Leu Cys Gly
610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
        675                 680                 685

Cys Pro Pro Gly Leu Tyr Met Asp Glu Arg Gly Asp Cys Val Pro Lys
690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
        755                 760                 765

Pro Pro Met Val Lys Leu Val Cys Pro Ala Asp Asn Leu Arg Ala Glu
770                 775                 780
```

-continued

```
Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
            805                 810                 815

His Glu Asn Arg Cys Val Ala Leu Glu Arg Cys Pro Cys Phe His Gln
        820                 825                 830

Gly Lys Glu Tyr Ala Pro Gly Glu Thr Val Lys Ile Gly Cys Asn Thr
            835                 840                 845

Cys Val Cys Arg Asp Arg Lys Trp Asn Cys Thr Asp His Val Cys Asp
        850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Lys Arg Val Thr Ile Leu
            915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
        995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
    1070                1075                1080

Cys Ile  Tyr Asp Thr Cys Ser  Cys Glu Ser Ile Gly  Asp Cys Ala
    1085                1090                1095

Cys Phe  Cys Asp Thr Ile Ala  Ala Tyr Ala His Val  Cys Ala Gln
    1100                1105                1110

His Gly  Lys Val Val Thr Trp  Arg Thr Ala Thr Leu  Cys Pro Gln
    1115                1120                1125

Ser Cys  Glu Glu Arg Asn Leu  Arg Glu Asn Gly Tyr  Glu Cys Glu
    1130                1135                1140

Trp Arg  Tyr Asn Ser Cys Ala  Pro Ala Cys Gln Val  Thr Cys Gln
    1145                1150                1155

His Pro  Glu Pro Leu Ala Cys  Pro Val Gln Cys Val  Glu Gly Cys
    1160                1165                1170

His Ala  His Cys Pro Pro Gly  Lys Ile Leu Asp Glu  Leu Leu Gln
    1175                1180                1185
```

-continued

```
Thr Cys Val Asp Pro Glu Asp Cys Pro Val Cys Glu Val Ala Gly
    1190                1195                1200
Arg Arg Phe Ala Ser Gly Lys Lys Val Thr Leu Asn Pro Ser Asp
    1205                1210                1215
Pro Glu His Cys Gln Ile Cys His Cys Asp Val Val Asn Leu Thr
    1220                1225                1230
Cys Glu Ala Cys Gln Glu Pro Gly Gly Leu Val Val Pro Pro Thr
    1235                1240                1245
Asp Ala Pro Val Ser Pro Thr Thr Leu Tyr Val Glu Asp Ile Ser
    1250                1255                1260
Glu Pro Pro Leu His Asp Phe Tyr Cys Ser Arg Leu Leu Asp Leu
    1265                1270                1275
Val Phe Leu Leu Asp Gly Ser Ser Arg Leu Ser Glu Ala Glu Phe
    1280                1285                1290
Glu Val Leu Lys Ala Phe Val Val Asp Met Met Glu Arg Leu Arg
    1295                1300                1305
Ile Ser Gln Lys Trp Val Arg Val Ala Val Val Glu Tyr His Asp
    1310                1315                1320
Gly Ser His Ala Tyr Ile Gly Leu Lys Asp Arg Lys Arg Pro Ser
    1325                1330                1335
Glu Leu Arg Arg Ile Ala Ser Gln Val Lys Tyr Ala Gly Ser Gln
    1340                1345                1350
Val Ala Ser Thr Ser Glu Val Leu Lys Tyr Thr Leu Phe Gln Ile
    1355                1360                1365
Phe Ser Lys Ile Asp Arg Pro Glu Ala Ser Arg Ile Thr Leu Leu
    1370                1375                1380
Leu Met Ala Ser Gln Glu Pro Gln Arg Met Ser Arg Asn Phe Val
    1385                1390                1395
Arg Tyr Val Gln Gly Leu Lys Lys Lys Lys Val Ile Val Ile Pro
    1400                1405                1410
Val Gly Ile Gly Pro His Ala Asn Leu Lys Gln Ile Arg Leu Ile
    1415                1420                1425
Glu Lys Gln Ala Pro Glu Asn Lys Ala Phe Val Leu Ser Ser Val
    1430                1435                1440
Asp Glu Leu Glu Gln Gln Arg Asp Glu Ile Val Ser Tyr Leu Cys
    1445                1450                1455
Asp Leu Ala Pro Glu Ala Pro Pro Pro Thr Leu Pro Pro Asp Met
    1460                1465                1470
Ala Gln Val Thr Val Gly Pro Gly Leu Leu Gly Val Ser Thr Leu
    1475                1480                1485
Gly Pro Lys Arg Asn Ser Met Val Leu Asp Val Ala Phe Val Leu
    1490                1495                1500
Glu Gly Ser Asp Lys Ile Gly Glu Ala Asp Phe Asn Arg Ser Lys
    1505                1510                1515
Glu Phe Met Glu Glu Val Ile Gln Arg Met Asp Val Gly Gln Asp
    1520                1525                1530
Ser Ile His Val Thr Val Leu Gln Tyr Ser Tyr Met Val Thr Val
    1535                1540                1545
Glu Tyr Pro Phe Ser Glu Ala Gln Ser Lys Gly Asp Ile Leu Gln
    1550                1555                1560
Arg Val Arg Glu Ile Arg Tyr Gln Gly Gly Asn Arg Thr Asn Thr
    1565                1570                1575
Gly Leu Ala Leu Arg Tyr Leu Ser Asp His Ser Phe Leu Val Ser
```

-continued

```
           1580               1585               1590
Gln Gly Asp Arg Glu Gln Ala Pro Asn Leu Val Tyr Met Val Thr
    1595               1600               1605
Gly Asn Pro Ala Ser Asp Glu Ile Lys Arg Leu Pro Gly Asp Ile
    1610               1615               1620
Gln Val Val Pro Ile Gly Val Gly Pro Asn Ala Asn Val Gln Glu
    1625               1630               1635
Leu Glu Arg Ile Gly Trp Pro Asn Ala Pro Ile Leu Ile Gln Asp
    1640               1645               1650
Phe Glu Thr Leu Pro Arg Glu Ala Pro Asp Leu Val Leu Gln Arg
    1655               1660               1665
Cys Cys Ser Gly Glu Gly Leu Gln Ile Pro Thr Leu Ser Pro Ala
    1670               1675               1680
Pro Asp Cys Ser Gln Pro Leu Asp Val Ile Leu Leu Leu Asp Gly
    1685               1690               1695
Ser Ser Ser Phe Pro Ala Ser Tyr Phe Asp Glu Met Lys Ser Phe
    1700               1705               1710
Ala Lys Ala Phe Ile Ser Lys Ala Asn Ile Gly Pro Arg Leu Thr
    1715               1720               1725
Gln Val Ser Val Leu Gln Tyr Gly Ser Ile Thr Thr Ile Asp Val
    1730               1735               1740
Pro Trp Asn Val Val Pro Glu Lys Ala His Leu Leu Ser Leu Val
    1745               1750               1755
Asp Val Met Gln Arg Glu Gly Gly Pro Ser Gln Ile Gly Asp Ala
    1760               1765               1770
Leu Gly Phe Ala Val Arg Tyr Leu Thr Ser Glu Met His Gly Ala
    1775               1780               1785
Arg Pro Gly Ala Ser Lys Ala Val Val Ile Leu Val Thr Asp Val
    1790               1795               1800
Ser Val Asp Ser Val Asp Ala Ala Ala Asp Ala Ala Arg Ser Asn
    1805               1810               1815
Arg Val Thr Val Phe Pro Ile Gly Ile Gly Asp Arg Tyr Asp Ala
    1820               1825               1830
Ala Gln Leu Arg Ile Leu Ala Gly Pro Ala Gly Asp Ser Asn Val
    1835               1840               1845
Val Lys Leu Gln Arg Ile Glu Asp Leu Pro Thr Met Val Thr Leu
    1850               1855               1860
Gly Asn Ser Phe Leu His Lys Leu Cys Ser Gly Phe Val Arg Ile
    1865               1870               1875
Cys Met Asp Glu Asp Gly Asn Glu Lys Arg Pro Gly Asp Val Trp
    1880               1885               1890
Thr Leu Pro Asp Gln Cys His Thr Val Thr Cys Gln Pro Asp Gly
    1895               1900               1905
Gln Thr Leu Leu Lys Ser His Arg Val Asn Cys Asp Arg Gly Leu
    1910               1915               1920
Arg Pro Ser Cys Pro Asn Ser Gln Ser Pro Val Lys Val Glu Glu
    1925               1930               1935
Thr Cys Gly Cys Arg Trp Thr Cys Pro Cys Val Cys Thr Gly Ser
    1940               1945               1950
Ser Thr Arg His Ile Val Thr Phe Asp Gly Gln Asn Phe Lys Leu
    1955               1960               1965
Thr Gly Ser Cys Ser Tyr Val Leu Phe Gln Asn Lys Glu Gln Asp
    1970               1975               1980
```

```
Leu Glu Val Ile Leu His Asn Gly Ala Cys Ser Pro Gly Ala Arg
    1985                1990                1995

Gln Gly Cys Met Lys Ser Ile Glu Val Lys His Ser Ala Leu Ser
    2000                2005                2010

Val Glu Leu His Ser Asp Met Glu Val Thr Val Asn Gly Arg Leu
    2015                2020                2025

Val Ser Val Pro Tyr Val Gly Gly Asn Met Glu Val Asn Val Tyr
    2030                2035                2040

Gly Ala Ile Met His Glu Val Arg Phe Asn His Leu Gly His Ile
    2045                2050                2055

Phe Thr Phe Thr Pro Gln Asn Asn Glu Phe Gln Leu Gln Leu Ser
    2060                2065                2070

Pro Lys Thr Phe Ala Ser Lys Thr Tyr Gly Leu Cys Gly Ile Cys
    2075                2080                2085

Asp Glu Asn Gly Ala Asn Asp Phe Met Leu Arg Asp Gly Thr Val
    2090                2095                2100

Thr Thr Asp Trp Lys Thr Leu Val Gln Glu Trp Thr Val Gln Arg
    2105                2110                2115

Pro Gly Gln Thr Cys Gln Pro Ile Leu Glu Glu Gln Cys Leu Val
    2120                2125                2130

Pro Asp Ser Ser His Cys Gln Val Leu Leu Leu Pro Leu Phe Ala
    2135                2140                2145

Glu Cys His Lys Val Leu Ala Pro Ala Thr Phe Tyr Ala Ile Cys
    2150                2155                2160

Gln Gln Asp Ser Cys His Gln Glu Gln Val Cys Glu Val Ile Ala
    2165                2170                2175

Ser Tyr Ala His Leu Cys Arg Thr Asn Gly Val Cys Val Asp Trp
    2180                2185                2190

Arg Thr Pro Asp Phe Cys Ala Met Ser Cys Pro Pro Ser Leu Val
    2195                2200                2205

Tyr Asn His Cys Glu His Gly Cys Pro Arg His Cys Asp Gly Asn
    2210                2215                2220

Val Ser Ser Cys Gly Asp His Pro Ser Glu Gly Cys Phe Cys Pro
    2225                2230                2235

Pro Asp Lys Val Met Leu Glu Gly Ser Cys Val Pro Glu Glu Ala
    2240                2245                2250

Cys Thr Gln Cys Ile Gly Glu Asp Gly Val Gln His Gln Phe Leu
    2255                2260                2265

Glu Ala Trp Val Pro Asp His Gln Pro Cys Gln Ile Cys Thr Cys
    2270                2275                2280

Leu Ser Gly Arg Lys Val Asn Cys Thr Thr Gln Pro Cys Pro Thr
    2285                2290                2295

Ala Lys Ala Pro Thr Cys Gly Leu Cys Glu Val Ala Arg Leu Arg
    2300                2305                2310

Gln Asn Ala Asp Gln Cys Cys Pro Glu Tyr Glu Cys Val Cys Asp
    2315                2320                2325

Pro Val Ser Cys Asp Leu Pro Pro Val Pro His Cys Glu Arg Gly
    2330                2335                2340

Leu Gln Pro Thr Leu Thr Asn Pro Gly Glu Cys Arg Pro Asn Phe
    2345                2350                2355

Thr Cys Ala Cys Arg Lys Glu Glu Cys Lys Arg Val Ser Pro Pro
    2360                2365                2370
```

```
Ser Cys Pro Pro His Arg Leu Pro Thr Leu Arg Lys Thr Gln Cys
2375                 2380                 2385

Cys Asp Glu Tyr Glu Cys Ala Cys Asn Cys Val Asn Ser Thr Val
    2390                 2395                 2400

Ser Cys Pro Leu Gly Tyr Leu Ala Ser Thr Ala Thr Asn Asp Cys
    2405                 2410                 2415

Gly Cys Thr Thr Thr Thr Cys Leu Pro Asp Lys Val Cys Val His
    2420                 2425                 2430

Arg Ser Thr Ile Tyr Pro Val Gly Gln Phe Trp Glu Glu Gly Cys
    2435                 2440                 2445

Asp Val Cys Thr Cys Thr Asp Met Glu Asp Ala Val Met Gly Leu
    2450                 2455                 2460

Arg Val Ala Gln Cys Ser Gln Lys Pro Cys Glu Asp Ser Cys Arg
    2465                 2470                 2475

Ser Gly Phe Thr Tyr Val Leu His Glu Gly Glu Cys Cys Gly Arg
    2480                 2485                 2490

Cys Leu Pro Ser Ala Cys Glu Val Val Thr Gly Ser Pro Arg Gly
    2495                 2500                 2505

Asp Ser Gln Ser Ser Trp Lys Ser Val Gly Ser Gln Trp Ala Ser
    2510                 2515                 2520

Pro Glu Asn Pro Cys Leu Ile Asn Glu Cys Val Arg Val Lys Glu
    2525                 2530                 2535

Glu Val Phe Ile Gln Gln Arg Asn Val Ser Cys Pro Gln Leu Glu
    2540                 2545                 2550

Val Pro Val Cys Pro Ser Gly Phe Gln Leu Ser Cys Lys Thr Ser
    2555                 2560                 2565

Ala Cys Cys Pro Ser Cys Arg Cys Glu Arg Met Glu Ala Cys Met
    2570                 2575                 2580

Leu Asn Gly Thr Val Ile Gly Pro Gly Lys Thr Val Met Ile Asp
    2585                 2590                 2595

Val Cys Thr Thr Cys Arg Cys Met Val Gln Val Gly Val Ile Ser
    2600                 2605                 2610

Gly Phe Lys Leu Glu Cys Arg Lys Thr Thr Cys Asn Pro Cys Pro
    2615                 2620                 2625

Leu Gly Tyr Lys Glu Glu Asn Asn Thr Gly Glu Cys Cys Gly Arg
    2630                 2635                 2640

Cys Leu Pro Thr Ala Cys Thr Ile Gln Leu Arg Gly Gly Gln Ile
    2645                 2650                 2655

Met Thr Leu Lys Arg Asp Glu Thr Leu Gln Asp Gly Cys Asp Thr
    2660                 2665                 2670

His Phe Cys Lys Val Asn Glu Arg Gly Glu Tyr Phe Trp Glu Lys
    2675                 2680                 2685

Arg Val Thr Gly Cys Pro Pro Phe Asp Glu His Lys Cys Leu Ala
    2690                 2695                 2700

Glu Gly Gly Lys Ile Met Lys Ile Pro Gly Thr Cys Cys Asp Thr
    2705                 2710                 2715

Cys Glu Glu Pro Glu Cys Asn Asp Ile Thr Ala Arg Leu Gln Tyr
    2720                 2725                 2730

Val Lys Val Gly Ser Cys Lys Ser Glu Val Glu Val Asp Ile His
    2735                 2740                 2745

Tyr Cys Gln Gly Lys Cys Ala Ser Lys Ala Met Tyr Ser Ile Asp
    2750                 2755                 2760

Ile Asn Asp Val Gln Asp Gln Cys Ser Cys Cys Ser Pro Thr Arg
```

| | 2765 | | | | | 2770 | | | | | 2775 | | | |
|---|---|---|---|---|---|---|---|---|---|---|---|---|---|---|
| Thr | Glu | Pro | Met | Gln | Val | Ala | Leu | His | Cys | Thr | Asn | Gly | Ser | Val |
| | 2780 | | | | | 2785 | | | | | 2790 | | | |
| Val | Tyr | His | Glu | Val | Leu | Asn | Ala | Met | Glu | Cys | Lys | Cys | Ser | Pro |
| | 2795 | | | | | 2800 | | | | | 2805 | | | |
| Arg | Lys | Cys | Ser | Lys | | | | | | | | | | |
| | 2810 | | | | | | | | | | | | | |